US009460632B2

(12) United States Patent
Watterson

(10) Patent No.: US 9,460,632 B2
(45) Date of Patent: Oct. 4, 2016

(54) SYSTEM AND METHOD FOR REWARDING PHYSICAL ACTIVITY

(71) Applicant: ICON Health & Fitness, Inc., Mendon, UT (US)

(72) Inventor: Scott R. Watterson, Logan, UT (US)

(73) Assignee: ICON Health & Fitness, Inc., Logan, UT (US)

(*) Notice: Subject to any disclaimer, the term of this patent is extended or adjusted under 35 U.S.C. 154(b) by 357 days.

(21) Appl. No.: 13/911,706

(22) Filed: Jun. 6, 2013

(65) Prior Publication Data

US 2013/0330694 A1 Dec. 12, 2013

Related U.S. Application Data

(60) Provisional application No. 61/656,768, filed on Jun. 7, 2012.

(51) Int. Cl.
*G09B 19/00* (2006.01)
*A61B 5/00* (2006.01)
*A61B 5/11* (2006.01)

(52) U.S. Cl.
CPC ............ *G09B 19/00* (2013.01); *A61B 5/0022* (2013.01); *A61B 5/1118* (2013.01)

(58) Field of Classification Search
CPC ............ A61B 5/1118; A61B 5/0022; A61B 2562/0219; G09B 19/00
USPC .................................................. 434/247–248
See application file for complete search history.

(56) References Cited

U.S. PATENT DOCUMENTS

| 5,456,648 A * | 10/1995 | Edinburg ........... A63B 22/0007 434/247 |
| 7,766,794 B2 | 8/2010 | Oliver et al. |
| 7,955,219 B2 | 6/2011 | Birrell et al. |
| 8,109,858 B2 | 2/2012 | Redmann |
| 8,506,458 B2 | 8/2013 | Dugan |
| 8,838,471 B1 * | 9/2014 | Shum ................. A63B 24/0084 482/8 |
| 2003/0165802 A1 * | 9/2003 | Murphy .................... G09B 7/00 434/350 |
| 2008/0027673 A1 | 1/2008 | Trumm |
| 2008/0147502 A1 | 6/2008 | Baker |

* cited by examiner

Primary Examiner — Timothy A Musselman
(74) Attorney, Agent, or Firm — Maschoff Brennan

(57) ABSTRACT

A system incentivizes people to engage in physical activity. A person's physical activity may be monitored over a period of time. Such monitoring may occur by using a sensing device carried or worn by the user. In the system, one or more thresholds for physical activity are established. Information tracked using the sensing device can be compared to the thresholds. A percentage of physical activity relative to the threshold can be translated to a reward established for the physical activity, and the percentage may be used to determine a reward value for an electronic device relative to a full available value. Rewards may include times or amounts. Time values may indicate durations during which particular activities or devices may be used. Amount values may indicate an amount of a battery charge, a number of communications, a currency value, or other values relative to use of an electronic device.

13 Claims, 9 Drawing Sheets

SYSTEM AND METHOD FOR REWARDING PHYSICAL ACTIVITY

CROSS-REFERENCE TO RELATED APPLICATIONS

This application claims priority to and the benefit of U.S. Patent Application Ser. No. 61/656,768 filed on Jun. 7, 2012 and entitled "SYSTEM AND METHOD FOR REWARDING PHYSICAL ACTIVITY."

TECHNICAL FIELD

The present disclosure relates generally to systems and methods for exercising. More particularly, the present disclosure relates to systems and methods for encouraging exercise. More particularly still, the present disclosure relates to systems and methods for encouraging exercise by providing rewards based on physical activity levels.

BACKGROUND

Regular exercise is important for a number of reasons, including comprehensive health, weight control, muscle toning, and the correction and avoidance of cardiovascular conditions. Indeed, there are well-known correlations between the amount of exercise a person engages in and the individual's physical as well as mental health. Estimates indicate that over two million people die prematurely each year in the United States as a result of causes that are attributable to a lack of sufficient physical exercise.

Despite the well-known importance of exercise, motivating people to exercise continues to be a significant challenge. Indeed, boredom is often cited as the primary obstacle to exercise. To help combat the boredom, and maintain a person's motivation level to exercise, portable music devices have often been used in connection with performance of an exercise program. Example portable music devices have in the past included portable radios, portable cassette and compact disk players, and more recently have included mp3 players and other similar devices that store digital copies of audio files. As a person exercises, the person can play music or other audio information to increase the person's interest in continuing interest.

While music has often been helpful for some people to avoid or mitigate boredom during exercise, it often does not itself provide a significant incentive to exercise. Indeed, modern devices such as smart phones, portable media players (e.g., the IPOD TOUCH® available from Apple Inc.), laptops, e-readers, tablet computing devices, and the like allow music to be available almost anywhere, whether stored directly on the device or streamed over a wireless network. A person simply doesn't need to exercise to listen to music as they may listen to music while doing other, less strenuous activities. Further, the same devices that often allow music to be available anywhere often are integrated with other capabilities. Such capabilities may include video, communication (e.g., video chat, instant messaging, text messaging, telephone, etc.), video game, and other capabilities. Teenagers and even younger children now often carry such devices, and can find entertainment with such devices that not only provides little incentive to exercise, but distracts them from exercising.

An example of a system for incentivizing people to exercise, and particularly for incentivizing children to exercise, is found in U.S. Patent Publication No. 2006/0025282, in which an exercise computer monitors the exercise performed by a child. The exercise computer may be portable and wearable. When the child performs well on certain exercises, or exercises regularly, the child may be rewarded. Example rewards include video games, cartoons, music, and merchant coupons. Additionally, the exercise computer may monitor the child's progress and skills and provide motivation and advice.

In addition, other related exercise systems, devices and methods for motivating people to exercise include those in U.S. Pat. Nos. 5,456,648, 7,955,219, U.S. Patent Publication No. 2008/0027673, U.S. Patent Publication No. 2008/0147502, U.S. Patent Publication No. 2009/0118100, and U.S. Patent Publication No. 2011/0275483.

SUMMARY OF THE DISCLOSURE

In one aspect of the present disclosure, a method for incentivizing physical activity includes tracking a person's physical activity over a period of time. The tracked physical activity may be compared to a threshold. A reward is identified for meeting the threshold. If the tracked physical activity is less than the threshold, a reward that is provided or authorized may be scaled to be proportional to the reward identified for meeting the threshold.

Another aspect of the disclosure that may be included in any combination with other aspects disclosed herein may include performing a method for incentivizing physical activity using a computing system having one or more processors.

Yet another aspect of the disclosure that may be included in any combination with other aspects disclosed herein may include tracking a person's physical activity using a sensing device.

Yet another aspect of the disclosure that may be included in any combination with other aspects disclosed herein may include using a sensing device carried or worn by a person.

Yet another aspect of the disclosure that may be included in any combination with other aspects disclosed herein may include tracking physical activity that includes a number of calories burned.

Yet another aspect of the disclosure that may be included in any combination with other aspects disclosed herein may include comparing a number of calories burned to a threshold number of calories burned.

Yet another aspect of the disclosure that may be included in any combination with other aspects disclosed herein may include a threshold and/or tracked physical activity that includes distance or duration information.

Yet another aspect of the disclosure that may be included in any combination with other aspects disclosed herein may include comparing physical activity to multiple thresholds.

Yet another aspect of the disclosure that may be included in any combination with other aspects disclosed herein may include comparing physical activity to multiple thresholds, the multiple thresholds being associated with the same reward.

Yet another aspect of the disclosure that may be included in any combination with other aspects disclosed herein may include comparing physical activity to multiple thresholds, at least some of the thresholds corresponding to different rewards.

Yet another aspect of the disclosure that may be included in any combination with other aspects disclosed herein may include comparing physical activity to a maximum threshold.

Yet another aspect of the disclosure that may be included in any combination with other aspects disclosed herein may include providing a reward associated with use of an electronic device.

Yet another aspect of the disclosure that may be included in any combination with other aspects disclosed herein may include a reward for use of an electronic device including a battery charge of the electronic device.

Yet another aspect of the disclosure that may be included in any combination with other aspects disclosed herein may include authorizing or providing a reward that is less than a full battery charge of an electronic device.

Yet another aspect of the disclosure that may be included in any combination with other aspects disclosed herein may include restricting charging of a battery based on a proportion of a person's physical activity relative to a threshold.

Yet another aspect of the disclosure that may be included in any combination with other aspects disclosed herein may include authorizing or providing a reward for use of an electronic device that includes talk time, text messaging, email messaging, or video game playing time.

Yet another aspect of the disclosure that may be included in any combination with other aspects disclosed herein may include authorizing or providing a reward that includes educational credit.

Yet another aspect of the disclosure that may be included in any combination with other aspects disclosed herein may include identifying multiple rewards corresponding to a threshold.

Yet another aspect of the disclosure that may be included in any combination with other aspects disclosed herein may include identifying multiple rewards for a threshold, the various rewards corresponding to multiple electronic devices.

Yet another aspect of the disclosure that may be included in any combination with other aspects disclosed herein may include authorizing multiple rewards redeemable on different electronic devices, where redeemable rewards are collectively proportional to tracked physical activity relative to a threshold.

Yet another aspect of the disclosure that may be included in any combination with other aspects disclosed herein may include computer-readable media storing instructions that can be executed by one or more processors to cause a computing system or device to perform a method for incentivizing physical activity.

Yet another aspect of the disclosure that may be included in any combination with other aspects disclosed herein may include receiving a request to use an electronic device.

Yet another aspect of the disclosure that may be included in any combination with other aspects disclosed herein may include accessing information about a reward based on physical activity of a person, and the reward being associated with restricted use of the electronic device.

Yet another aspect of the disclosure that may be included in any combination with other aspects disclosed herein may include displaying a portion of a reward available for redemption on an electronic device.

Yet another aspect of the disclosure that may be included in any combination with other aspects disclosed herein may include monitoring use of an electronic device relative to a reward.

Yet another aspect of the disclosure that may be included in any combination with other aspects disclosed herein may include sending a message to an administrator computing device that indicated what portion of a reward is redeemed at an electronic device.

Yet another aspect of the disclosure that may be included in any combination with other aspects disclosed herein may include providing encouragement to a person to engage in additional physical activity to increase an available reward.

Yet another aspect of the disclosure that may be included in any combination with other aspects disclosed herein may include using current information to provide encouragement.

BRIEF DESCRIPTION OF THE DRAWINGS

The accompanying drawings illustrate various embodiments of the present systems and methods and are a part of the specification. The illustrated embodiments are merely examples of the present systems and methods and do not limit the scope thereof. Throughout the drawings, the same reference number designates similar, but not necessarily identical, elements.

DETAILED DESCRIPTION

A system for incentivizing people to exercise is disclosed herein. Specifically, embodiments of the present disclosure include a system that may monitor exercise that a person performs over a given time period (e.g., daily, weekly, monthly, etc.). The exercise system may use a sensing device that detects the exercise done. Information logged by the sensing device can be correlated with rewards available for meeting exercise or health-related criteria. If the criteria is met, full rewards may be obtained. If the criteria is not met, no rewards or partial rewards may be provided. In some embodiments, the system may be managed by an administrator, such as a parent or educator. The system may monitor the exercise performed by a child or dependent, and incentives can relate to use of electronic devices available to the child or dependent, or to educational credit.

Figure 1:
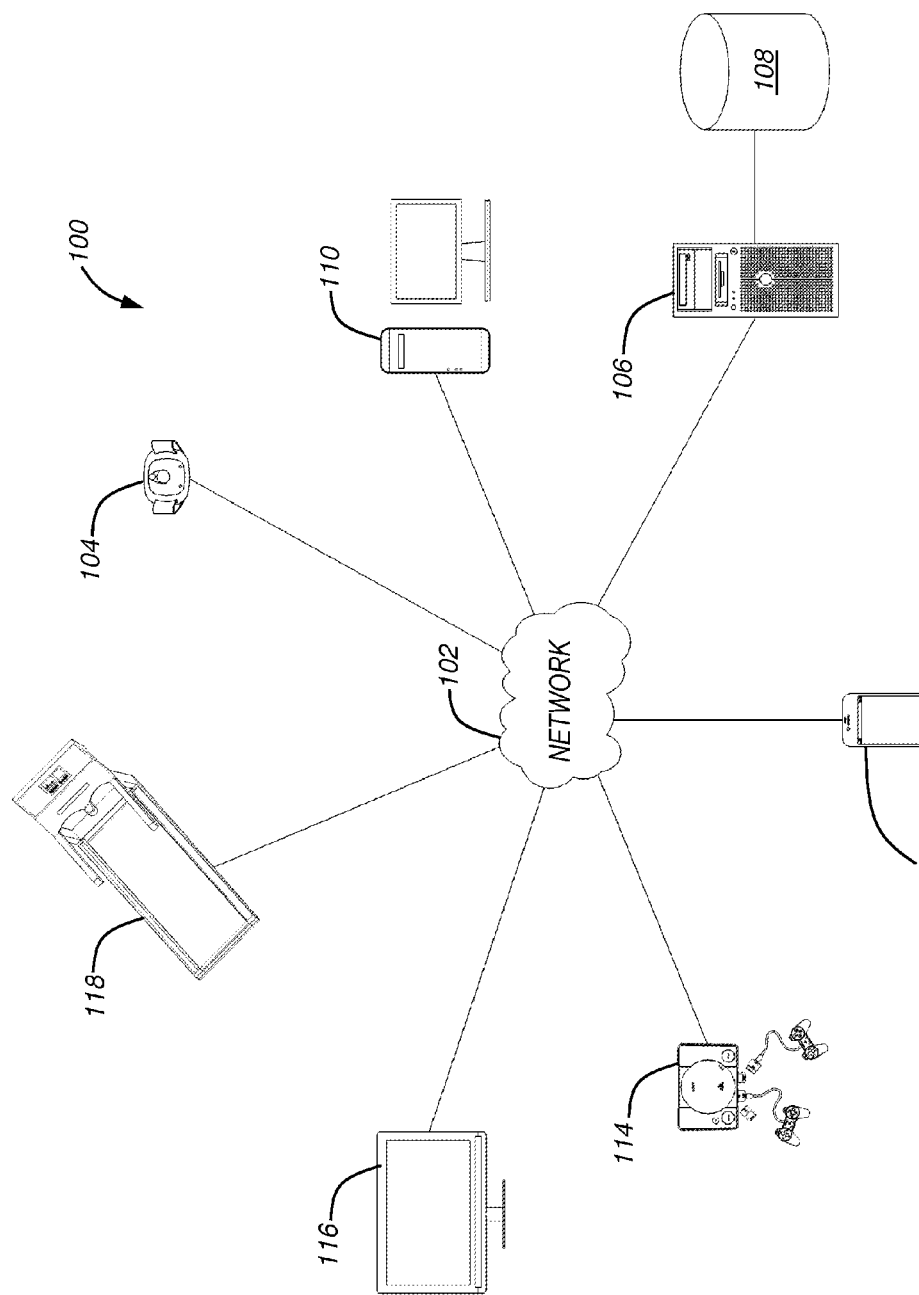
FIG. 1 schematically illustrates an example system that includes a sensing device and one or more computing devices communicating over a network, in accordance with one embodiment of the present disclosure.

In FIG. 1 illustrates an example system 100 that may include multiple devices or components for managing exercise incentives in accordance with embodiments of the present disclosure. As part of the system 100, a network 102 may be provided to facilitate communication between one or more devices or components (e.g., devices 104-118). The network 102 may be any suitable network, and may include a wireless network, a wired network, or some combination thereof. In some embodiments, the network 102 may include multiple networks. For instance, the network 102 may include the Internet, a local access network, a wide access network, a CDMA network, a GSM network, an LTE network, a Wi-Fi network (e.g., 802.11 communication network), or other types of local or even global networks, or any combination of the foregoing. It should be appreciated in view of the disclosure herein that some devices 104-116 may communicate using different networks or protocols, but that using the combined network 102, any device 104-118 may potentially have such communicates relayed to any other device 104-118.

The illustrated system 100 includes various devices 104-118 that may communicate through the network 102. By way of illustration, the system 100 of FIG. 1 includes an example sensing device 104 and computing device 106. In some embodiments the computing device 106 may be a server, although the computing device 106 may instead by a personal computing device or satisfy some other purpose.

The sensing device 104 may generally be utilized to sense and track physical activity of a user. In some embodiments, for instance, the sensing device 104 may include one or more sensors to track movement, heart rate, metabolism or other items related to exercise or a user's health and well being. In addition to or in lieu of such sensors, the sensing device 104 may also include input components. For instance, the sensing device 104 may include a user interface to allow a user to input information. Information that is input may include information related to exercise (e.g., start/end times, distance, workout type, etc.), food consumption (e.g., calories consumed), or the like.

The sensing device 104 device may be used in any number of different manners by a user. For instance, in one embodiment the sensing device 104 may be worn by the user. An example sensing device 104 could be worn on the wrist or ankle, around the chest, or in another manner. In such an embodiment, the sensing device 104 could potentially obtain information related to the heart rate of the user (e.g., by measuring a pulse), perspiration levels, and the like. In other embodiments, the sensing device 104 may be worn or used in other manners. An example sensing device 104 could, for instance, be placed in a user's pocket. The sensing device 104 may include suitable sensors or components to determine information such as the number of steps taken, the distance moved, the altitude climbed, change in physical location, and the like. In some embodiments, a sensing device 104 may be integrated into another component or device (e.g., a telephone or portable media player), although it may also be a separate device.

In accordance with one aspect of the present disclosure, the sensing device 104 is worn, carried, or otherwise used by a person throughout the day. While with the person, the sensing device 104 tracks the physical activity of the person. Information related to the physical activity may then be used in a manner that may be learned by a review of the disclosure herein.

Information from the sensing device 104 may also be communicated through the network 102, or by other means, to other devices or components 106-118 of the system 100. In one example, information obtained, calculated or otherwise accessed by the sensing device 104 may be communicated to the computing device 106. The computing device 106 may act as a server that collects such information on behalf of the user of the sensing device 104, and potentially on behalf of a number of different people. For instance, the computing device 106 may be within a home and each member of a family may have a corresponding sensing device 104 for obtaining information communicated to the computing device 106. On a larger scale, the computing device 106 may operate in connection with a service in which people at remote locations dispersed across a country or even the world can have information from corresponding sensing devices 104 stored at or accessible to the computing device 106. The computing device 106 may actually be a collection of multiple devices and need not be a single device.

Optionally, the computing device 106 may be used to determine a correlation between physical activity as reported by the sensing device 104 and rewards available to a user of the sensing device. More particularly, in one embodiment of the present disclosure the computing device 106 may store information related to rewards available to a user and the goals that may be met to satisfy the requirements for such rewards. As further discussed herein, in some cases the computing device may store information for determining partial rewards when a goal is not completely satisfied but progress towards the goal is made.

Although such information may be stored by the computing device 106, in other embodiments the computing device 106 may store the information remotely or in other locations, or access the information from other sources. In FIG. 1, for instance, a data store 108 is shown as being accessible to the computing device 106. According to one embodiment, the computing device 106 may be a server and the data store 108 may be a dedicated database accessible by the server. In other embodiments, the data store 108 may be integrated within the computing device 106 or accessible by, or even integrated within, other components of the system 100.

The system 100 may also include a variety of additional components. For instance, the system 100 is shown as including an additional computing device 110 in communication with the network 100. The computing device 110 is illustrative of a personal computer, office computer, laptop, tablet, or other computing device that a person may access. As shown in FIG. 1, the computing device 110 may communicate through the network with other devices, potentially including the sensing device 104 and/or the computing device 106. Thus, information obtained by the sensing device 104 about a person's physical activity, or information about rewards associated with the physical activity, may be accessible to the personal computer 110.

As discussed herein, an aspect of the present disclosure includes providing rewards to people who engage in physical activity, and thereby incentivizing them to continue exercising. According to one embodiment, rewards may be obtained in the form of access to electronic devices, or access to applications or programs on electronic devices. Thus, in one embodiment, the personal computer 110 may be a device to which access is at least partially based on rewards in an exercise incentive system such as system 100. For instance, if a threshold level of exercise is satisfied for a day, a user may be allowed to login to and use the computing device 110, or to play video games on, or otherwise use applications and programs on the computing device 110. If the user has not satisfied the threshold level of exercise, access to the computing device 110, or portions thereof, may be unavailable, or may be limited.

Other electronic devices that may be subject to limitations based on physical activity include portable electronic device 112, gaming system 114, and television 116. It should be appreciated in view of the disclosure herein that any number of additional devices could have been included and may also be subjected to limitations based on physical exercise.

The portable electronic device 112 is generally representative of a mobile device such as a mobile telephone, a portable media player, an e-reader, a tablet computing device, or any number of other computing or electronic devices that can be easily transported from one location to the next. In some cases, the portable electronic device 112 may be a so-called "smart phone" which includes not only telephone capabilities, but also other communication capabilities such as email, instant messaging, text messaging, video conferencing, and the like. Further or other applications of the portable electronic device 112 may include gaming programs, productivity applications, audio or video programs, and the like.

Gaming system 114 and television 116 may each also be devices that can be operated in connection with an exercise incentive system as described herein. Each device 114, 116 may communicate through the network (e.g., with computing device 106 or sensing device 104) to obtain information on a user's exercise. Based on the exercise performed, the user may or may not be granted access to play video games or watch television, or the time or available programs may be limited as desired. A greater explanation of manners of using devices 106-116 in connection with an exercise incentive program is provided below with respect to FIG. 2.

Also illustrated in FIG. 1 is an example exercise device 118. The exercise device 118 can take any of a number of different forms. The illustrated device 118, for instance, is a treadmill-type device, although other devices may include stationary bicycles, elliptical machines, steppers, rowers, weight systems, and the like. The exercise machine 118 may also optionally be connected to the network 102 to communicate with one or more other devices 104-116. In some cases the exercise device 118 may operate in addition to, or instead of, the sensing device 104 to provide information about a user's physical activity. For instance, a user may begin a workout using the exercise device 118. During the workout, or upon completion thereof, information about the workout (e.g., duration, distance, intensity, calories burned, average heart rate, etc.) may be communicated over the network 102. The information may be used by the computing system 106 to identify rewards available to the user, and such rewards may optionally be available for redemption on the computing devices 110-116. In other embodiments, the information from the exercise device 118 may be communicated to the devices 110-116. For instance, if a user wants to play a game using the gaming system 114, the gaming system 114 may request exercise information from the exercise device 118 (or computing device 106). The gaming system 114 may then determine if access should be provided, what type of access may be provided, how long to provide access, and the like.

While FIG. 1 illustrates a system in which each of numerous devices 104-118 may communicate through the network 102, the system 100 is illustrative only, and may be modified in any number of different manners. For instance, nothing in system 100 requires that all of the devices 104-118 maintain a connection with the network 102 at all times, or even that a particular type of communication system be used. Instead, devices 104-118 may selectively communicate through the network 102. Alternatively, some of the devices 104-118 may communicate with other of the devices 104-118 out-of-band relative to the network 102. For instance, the sensing device 104 may track physical activity. When a user wishes to provide information on his or her exercise to the system, or to obtain rewards for the activity, the user may use a physical cable to directly connect the sensing device 104 to a suitable device (e.g., computing system 110, portable electronic device 112, gaming system 114, or television 116), or use some other connection mechanism. Alternatively, a memory component (e.g., an SD card) of the sensing device 104 may be removed and connected to a desired device.

Figure 2:
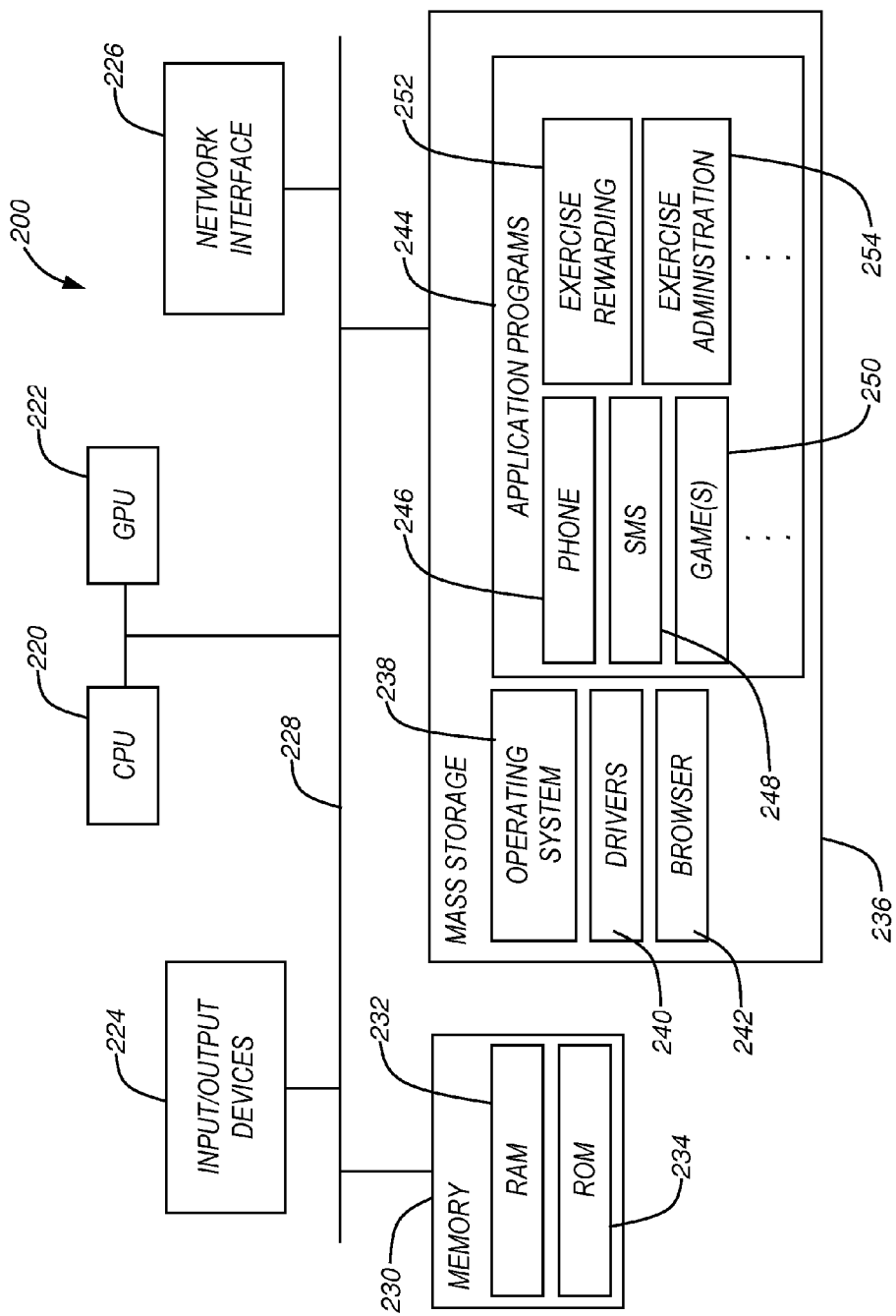
FIG. 2 schematically illustrates an example computing device usable in the system of FIG. 1, according to one embodiment of the present disclosure.

Turning now to FIG. 2, an example computing system 200 is schematically illustrated in greater detail. The computing system 200 of FIG. 2 generally represents a number of different devices that may be used in connection with the system 100 of FIG. 1, as well as devices that may be used to manage rewards and incentives on account of physical activity, or to provide activities that are restricted or awarded depending on physical activity. For instance, the computing system 200 of FIG. 2 may be used as the computing device 106 of FIG. 1, which device may access and/or store information related to the physical activity of one or more users. The computing system 200 may then be used to identify what rewards are available based on the activity and provide information to corresponding devices or systems so that rewards can be redeemed. Alternatively, the computing system 200 could instead be used as the portable electronic device 112 of FIG. 1, which device may obtain information from another source (e.g., sensing device 104 or computing device 106) to determine whether the user has redeemed rewards that relate to the use of the computing system. For instance, the computing system 200 may determine that based on a user's physical activity, the user has access to a certain amount of talk time, a certain number of emails or text messages, one or more games or other applications, application download programs, or even power capabilities. For instance, based on an available reward, the user may be given the ability to charge the portable electronic device 112 to a particular power level. As will be appreciated in view of the disclosure herein, other incentives are also available, including when the computing system 200 represents a gaming system, television, or other device.

In FIG. 2, the computing system 200 includes multiple components that may interact together over one or more communication channels. In this embodiment, for instance, the system 200 may include multiple processors. More particularly, the illustrated processors include a central processing unit (CPU) 220 and a graphics processing unit (GPU) 222. The CPU 220 may generally be a multi-purpose processor for use in carrying out instructions of computer programs of the system 200, including basic arithmetical, logical, input/output (I/O) operations, or the like. In contrast, the GPU 222 may be primarily dedicated to processing of visual or graphical information. In one example embodiment, the GPU 222 may be primarily dedicated to display of images and the like, and may be heavily used in video games. In other embodiments, a single processor or multiple different types of processors may be used other than, or in addition to, those illustrated in FIG. 2.

The CPU 220, GPU 222 or other processors may interact or communicate with one or more input/output (I/O) devices 224, a network interface 226, memory 230 and/or a mass storage device 236. One manner in which communication may occur is using a communication bus 228, although multiple communication busses or one or more other communication channels or interfaces may be used.

The CPU 220 and/or GPU 222 may generally include one or more processing components capable of executing computer-executable instructions received or stored by the system 200. For instance, the CPU 220 or GPU 222 may communicate with the input/output devices 224 using the communication bus 228. The input/output devices 224 may include ports, keyboards, a mouse, scanners, printers, display elements, touch screens, microphones or other audio input devices, speakers or other audio output devices, global positioning system (GPS) units, audio mixing devices, cameras, sensors, power supplies, other components, or any combination of the foregoing, at least some of which may provide input for processing by the CPU 220 or GPU 222, or which may receive information output from the processors 220, 222. Similarly, the network interface 226 may receive communications via a network (e.g., network 102 in FIG. 1). Received data may be transmitted over the bus 228 and processed in whole or in part by the processors 220, 222. Alternatively, data processed by the processors 220, 222 may be transmitted using the bus 228 or other system components to the network interface 226 for communication to another device or component connected over a network or other communication channel. The other device or component may be local or may be remote relative to the system 200 illustrated in FIG. 2.

The system 200 may also include memory 230 and mass storage 236. In general, the memory 230 may include both persistent and non-persistent storage, and in the illustrated embodiment the memory 230 is shown as including random access memory 232 and read only memory 234. Other types of memory or storage may also be included in memory 230. The mass storage 236 may generally be comprised of persistent storage in a number of different forms. Such forms may include a hard drive, flash-based storage, optical storage devices, magnetic storage devices, or other forms which are either permanently or removably coupled to the system 200, or in any combination of the foregoing. In some embodiments, an operating system 238 defining the general operating functions of the computing system 200, and which may be executed by the CPU 220, may be stored in the mass storage 236. Other example components stored in the mass storage 236 may include drivers 240, a browser 242 and application programs 244.

The term "drivers" is intended to broadly represent any number of programs, code, or other modules including Kernel extensions, extensions, libraries, or sockets. In general, the drivers 240 may be programs or include instructions that allow the computing system 200 to communicate with other components either within or peripheral to the computing system 200. For instance, in an embodiment where the I/O devices 224 include a display unit, the drivers 240 may store or access communication instructions indicating a manner in which data may be formatted to be displayed on the display unit. The browser 242 may be a program generally capable of interacting with the processors 220, 222, as well as the network interface 226 to browse programs or applications on the computing system 200 or to access resources available from a remote source. Such a remote source may optionally be available through a network or other communication channel. A browser 242 may generally be considered a type of application within applications 244, or may be considered a separate component as illustrated in FIG. 2. An example browser may be an Internet or web browser for accessing pages of resources available over the Internet or another global or other network.

The application programs 244 may include other programs or applications that may be used in the operation of the computing system 200. Examples of application programs 244 may include a telephone application 246, a text messaging application 248, one or more gaming applications 250, or virtually any other type of application. As will be appreciated by one of skill in the art in view of the disclosure herein, other types of applications 244 may provide other functions or capabilities, and may include email applications, calendar applications, productivity applications, music or video applications, map applications, and the like.

In at least one embodiment, the application programs 244 include an exercise rewarding application 252. The exercise rewarding program 252 may generally perform a number of different functions related to using exercise information to obtain rewards. For instance, the exercise rewarding program 252 may access exercise-related information and/or reward information. In some cases, the exercise rewarding program 252 may also provide information on the available rewards. More particularly, information may be provided to a user to know what rewards are available, or information may be provided to other systems or components to allow rewards to be redeemed. In one embodiment, for instance, the system 200 may use exercise information to determine that a reward is available for another device (e.g., a television) and then send a message to the other device to allow the other device to then provide the reward. Alternatively, the system 200 may be the device where the reward is redeemed in which case the system 200 may receive a message for providing the reward. In some cases, the device which determines what rewards are available is the same electronic device on which the reward is redeemed.

The exercise redeeming program 252 may also perform other functions. For instance, rewards may vary based on whether exercise meets certain goals or thresholds. If exercise is below a threshold, the exercise rewarding program 252 may provide information to a user to allow the user to know that additional exercise may be required for a reward, or that additional exercise may increase the available rewards. In other embodiments, third party information, such as weather, may be accessed to make suggestions to the user on what physical activities to engage in.

As an illustration, the exercise rewarding program 252 may determine that by engaging in some additional exercise the user may be able to increase his or her reward. Using the network interface 226, the exercise rewarding program 252 may access a third party data source that includes weather information. If the weather information indicates that the weather is suitable for outdoor activity, the exercise rewarding program 252 may provide a message indicating that an outdoor exercise activity would be available for some additional exercise. If the weather was not suitable for outdoor activity, a different message may suggest indoor weight lifting, yoga, treadmill, or other exercises.

As also shown in FIG. 2, the system 200 may additionally or alternatively include an exercise administration program 254. The exercise administration program 254 may generally be used to administer an incentive exercise incentive program. For instance, in some embodiments the exercise administration program 254 may be used to identify exercise goals or thresholds for a particular person, group of people, and the like. The exercise administration program 254 may further specify what rewards are available. Certain rewards may be associated with particular exercise activities or goals, and the correlation may be specified in the exercise administration program 254.

While the exercise administration program 254 and exercise rewarding program 252 are shown as being included on the same computing system 200, this is merely illustrative. In other embodiments, certain devices may include only one of the exercise administration program 254 or the exercise rewarding program 252. A gaming system, television, portable electronic device, or other electronic device, for instance, may have access thereto granted or limited based on rewards. Such a device may include only the exercise rewarding application 252 to govern how rewards are redeemed. The exercise rewarding application 252 may communicate with or use information from the exercise administration application 254; however, the exercise administration program 254 may reside elsewhere.

Figure 3:
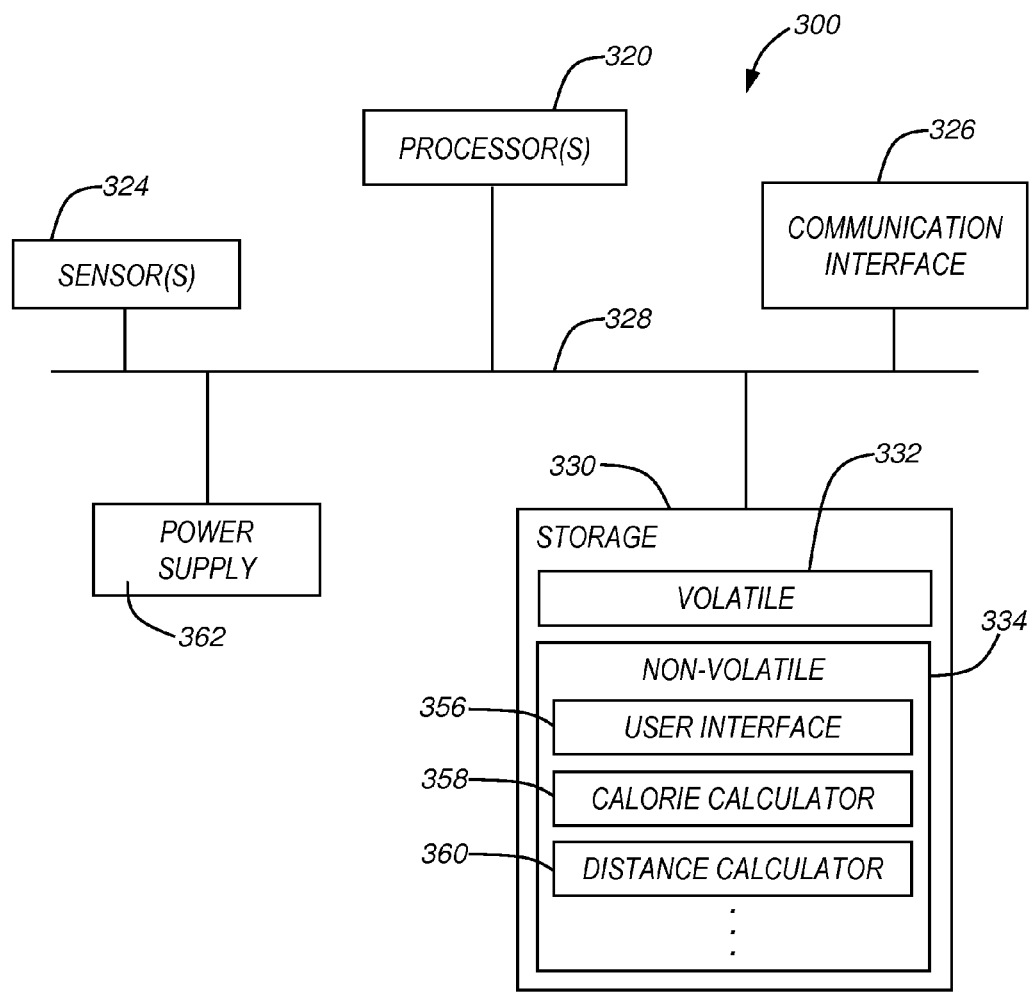
FIG. 3 schematically illustrates a sensing device usable in the system of FIG. 1, according to an embodiment of the present disclosure.

With reference now to FIG. 3, an example sensing device 300 is shown in additional detail. The sensing device 300 generally represents a personal device that may be worn or carried by a user to track exercise or fitness information; however, the sensing device 300 may be more broadly embodied in aspects of other devices, including exercise equipment and personal electronic devices.

The example sensing device 300 includes one or more processors 320 usable to process data or instructions and perform basic arithmetical, logical, input/output (I/O) operations, or the like. Information used by the processors 320 may be obtained from one or more sensors 324, from a communication interface 326, or from a memory component 330. The information may be obtained using a communication bus 328 connecting any or all of the processors 320, sensors 324, communication interface 326 or memory 330.

As shown in FIG. 3, the illustrated embodiment of a sensing device 300 contemplates the use of one or more sensors 324. The sensors 324 may be of any number of different types and can obtain a variety of different types of information. For instance, one example sensor of the sensors 324 may include a pedometer. A pedometer is a sensor that can count the steps taken by a person, and often includes detecting motion of a person's hips. Another type of sensor may include an accelerometer. An accelerometer can measure acceleration along a single axis or along multiple axes. In general, such measurements can be used to measure motion and vibrations. Different movement profiles may be produced for different activities. For instance, an accelerometer on a person who is walking or running may produce different readings than for a person who is lifting weights or swimming. The accelerometer may nonetheless measure the movement during any of these physical activities, and potentially can determine the type of activity producing the results.

Another type of sensor that may be provided in the sensors 324 may include an altimeter or a GPS unit. An altimeter measures changes in altitude, which may be helpful for activities such as hiking or climbing stairs. The altimeter can measure the elevation change so that the type or results of the activity can be identified. A GPS unit, in contrast, identifies location. Using satellite communication, the location of a person can be pinpointed, along with the change in position. A person who is walking, running, cycling or otherwise moving may thus have their location monitored to determine distance covered, speed, pace, and the like.

Still another type of sensor that may be used in the system 300 includes a heart rate monitor. The heart rate monitor can measure a pulse to determine how frequently a heart is beating. Such a measurement may indicate how strenuously a person is exercising, or may provide an indication as to a health condition. Another sensor usable in the system 300 may include a perspiration monitor and/or thermometer. Such sensors may be used to determine how much a person is sweating or the person's skin temperature, which can also be correlated with physical activity levels.

As discussed herein, information about a person's exercise or other physical activity may be provided to various components in a communication system. Optionally, the information that is obtained from the sensors 324 may be processed by the processors 320 and/or stored in memory 330. The memory 330 may include any of a number of different types, including both volatile memory 332 and non-volatile memory 334. The volatile memory 332 may generally be used to temporarily store information obtained by the sensors 324, processed by the processors 320, or communicated using the communication interface 326, or for other purposes. Other information stored more persistently may be stored on the non-volatile memory 334.

Information stored on the non-volatile memory 334 may include a user interface module 334. In some embodiments, the sensing device 330 may allow a user to input information not otherwise available from the sensors 324. The user interface 356 may, for instance, allow a user to identify a type of exercise being performed. The user interface component 356 may also allow a user to input other information, such as the type and/or quantity of food eaten, the user's size (e.g., height and weight), and other information.

Also stored in the non-volatile memory 334 of the sensing device 300 of FIG. 3 is a calorie calculation component 358. According to one example embodiment, the sensors 324 may obtain information about a person's physical activity. Information about the user's movement, heart rate, and the like may thus indicate when a person is exercising, how long they exercise for, and how strenuous the exercise is. The calorie calculation component 358 may use such information to determine how many calories a person burned during the exercise.

The calorie calculation component 358 may employ any of a number of different algorithms to provide an indication of the number of calories burned. Indeed, the number of calories burned during a given period of time can be dramatically different depending on the type of activity being performed, the size of the person performing the activity, and the intensity level with which the activity is performed. Thus, according to one embodiment, the calorie calculation component 358 uses each of multiple different algorithms to calculate calories burned.

By way of illustration, if the sensors 324 determine that a person is most likely walking or running, the calorie calculation component 358 may choose to use an algorithm such as the following:

$$C = \frac{w \cdot t}{19.658 - 0.993v}$$

In the above formula, C represents the number of calories burned, while w represents weight in pounds, t represents duration of exercise in minutes, and v represents the velocity. Other types of exercises may use other algorithms to estimate heart rate.

The calorie calculation component 358 may thus use different algorithms for different exercises. In other embodiments however, one algorithm may be used for all exercises or for multiple different types of exercises (e.g., for any exercise not having its own equation). Some examples of such algorithms may include a formula using a metabolic equivalent (MET). In other embodiments, indirect calorimetry (e.g., measuring differences in oxygen and carbon dioxide respiration to estimate heat generation) or predictive energy expenditure equations (e.g., Mifflin-St. Jeor, Harris-Benedict calculations) may be used to estimate the number of calories burned.

In addition to calculating calories burned, or as an alternative thereto, other calculations could be performed. FIG. 3, for instance, illustrates non-volatile memory 334 that includes a distance calculator 360. The distance calculator 360 may calculate the distance of travel for any of different exercises, and may do so based on information obtained from the sensors 324. As an example, if the sensors 324 include a pedometer, the number of steps taken along with calibration information for the user may be used to estimate the distance traveled over a period of time. Alternatively, the sensors 324 may include an accelerometer which can be used to measure speed, distance or direction of travel. In some cases, the sensors 324 may use a GPS device to obtain information that can be used by the distance calculator 360 to determine distance traveled.

Although not specifically illustrated in FIG. 3, the sensing device 300 may be used to determine a variety of other types of information. For instance, calculations may be performed to determine an average heart rate, a duration of a particular exercise or activity, or other information that can be directly or indirectly determined from the information gathered by the sensors 324.

As will be appreciated in view of the disclosure herein, information obtained using the sensors 324 and user interface 356 may thus be communicated to other components of the sensing system 300 (e.g., using the communication bus 328). The same information may also be communicated to other components outside of the sensing device 300, either in the same form as obtained, or in a processed form. By way of illustration, rather than passing information directly received by the sensors 324, the information may be processed using the processors 320 based on the calorie calculator 358, distance calculation 360, or some other module, and then communicated to another device or system using the communication interface 326. Moreover, raw or processed information may be communicated according to any of a number of different protocols. For instance, the communication interface 326 may use a wired connection (e.g., Ethernet) or wireless connection (e.g., Bluetooth, 802.11, etc.) to transfer information. In other embodiments, all or a portion of the storage 330 is removable (e.g., an SD card), so that information that is sensed or calculated can be stored and removed. The removed storage may then be connected to another device for use.

In some embodiments, the sensing device 300 is a portable device that may be worn or carried by a user. For instance, the sensing device 300 may have the form of a chip or watch so as to move with a user as they move from place to place and activity to activity. As a result, the activities throughout an entire day may be monitored and the calorie, distance, heart rate, or other information over that time may be monitored and aggregated. In such an embodiment, the sensing device 300 may include a power supply 362. The power supply 362 is optionally rechargeable or replaceable (e.g. a battery) that can power components such as the processors 320 and sensors 324 to enable operation of the sensing system 326.

In other embodiments, the sensing device 300 may be integrated into other equipment, such as a treadmill, exercise bicycle, or other type of indoor or outdoor exercise equipment, or in a portable electronic device (e.g., a smart phone). For such a device, there may continue to be a power supply 362. Optionally, the power supply 362 for such a device may be dedicated to the sensing components; however, the power supply 362 may also be a general power component providing power to any number of different components, including for display screens, input devices, motors, and the like.

Figure 4:
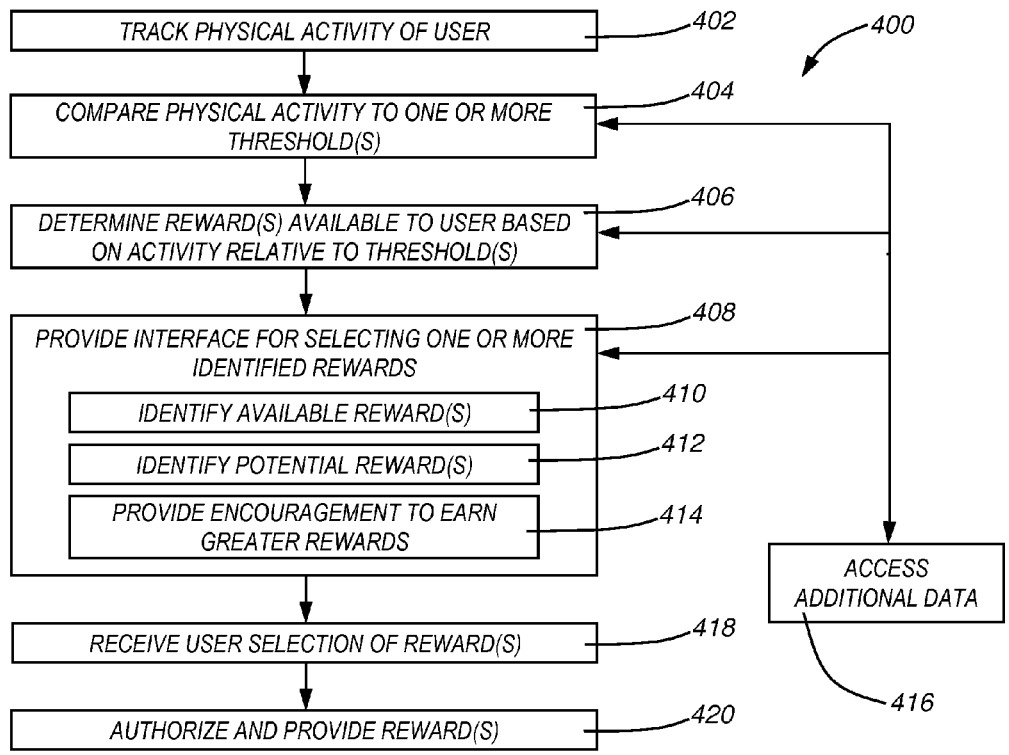
FIG. 4 illustrates a method for rewarding a person for engaging in physical exercise, in accordance with one embodiment of the present disclosure.

Turning now to FIG. 4, an example method 400 for rewarding a user for engaging in physical activity is described in additional detail. To provide an understanding of one example embodiment of how the method 400 may be performed, the method 400 will be described with reference to certain components of the devices and systems of FIGS. 1-3, although other systems, devices and components may also be used in performing the method 400 of FIG. 4.

According to one aspect of the present disclosure, the method 400 includes an act 402 of tracing the physical activity of a user. As discussed herein, tracking the physical activity of a user in act 402 may occur using any number of manners. In accordance with at least one embodiment, for instance, a user may wear or carry a sensing device (e.g., sensing device 104 or 300). The sensing device may then be used to track the user's movements or other activity during the day. Example sensing devices may therefore track information such as the number of steps taken, distance traveled, speed, type of exercise, heart rate, exercise duration (e.g., duration of exercise above a certain heart rate), or the like. According to at least some embodiments, information that is tracked may be used to calculate or determine other information. For instance, information about the speed, heart rate, type of exercise and the like may be used to calculate the number of calories the user of the sending device is estimated to have burned during an activity or over a period of time. Of course, other methods of tracking the activity of a user in act 402 may also be used. For instance, a user may manually enter exercise information into a logging program or may use an exercise device which can track and potentially transmit such information to a logging program.

Regardless of the particular manner in which physical activity of a user is tracked in act 402, the tracked information may be used to determine rewards for the user as discussed herein. In accordance with one embodiment, rewards are determined by, at least in part, comparing the physical activity that is tracked to one or more thresholds. The thresholds that are set may correspond to physical activity information that is tracked, whether directly by a sensor, calculated from sensed information, or otherwise input or obtained. As an example, a threshold may be the number of calories that should be burned during a day. A sensing device used in tracking the user's physical activity in act 402 may estimate a number of calories burned, or provide information to another system component that can determine the calories burned information for a user. The number of calories burned according to the tracked physical activity information may be compared to the threshold value for calories burned in act 404. Based on the comparison, the method 400 may be used to then determine if the user's activity met the threshold (i.e., by meeting or exceeding the threshold), or how close the user came to meeting the threshold (e.g., determining that the calories burned was some percentage of the threshold). Of course, a similar comparison may be done for thresholds set for other physical activity information such as distance, number of steps, duration of exercise, and the like.

While the above description describes a comparison to a single threshold, there may be multiple thresholds to which the physical activity is compared in act 404. For instance, there may be multiple thresholds for a single physical activity category, such as calories burned, or thresholds may be in different physical activity categories.

The method 400 may further include determining what reward or rewards are available to a user base don their activity relative to the one or more thresholds, as shown in act 406 of method 400. As discussed herein, there are a number of different types of rewards that are available, and the manner of providing the rewards based on the threshold levels of physical activity may vary based on the type of reward, or may be applied for all types of rewards. For instance, continuing with the example of tracking calories burned and comparing the calories burned relative to a threshold value, the method 400 may determine that the user has exceeded the threshold. In that case, a full reward of a given type may be available to the user. By way of illustration, for meeting the threshold number of calories burned in a twenty-four hour period, a user may be allowed to fully charge his or her cellular phone, portable media player, or other portable electronic device. Additional or alternative rewards that may be available include a certain amount of talk time on a cellular phone, a particular number of text messages, a duration of time to watch television or play computer games, a specified cash value for downloading applications for a portable computing device, or the like.

In contrast, if the user does not meet the threshold level for calories burned, the rewards as determined in act 406 may be different than the maximum available rewards. As an illustration, if during one day a user burns only seventy-five percent of the threshold value of calories, the user may receive no rewards. Alternatively, a user burning seventy-five percent of the threshold value of calories may receive a reduced reward relative to the full reward. In one embodiment, determining the rewards available in act 406 may provide rewards proportional to the full reward. Thus, if a reward is for a full charge of a portable electronic device when the threshold is satisfied, a charge of seventy-five percent may provided as a reward when the user reaches seventy-five percent of the threshold. In other embodiments, other schemes may be provided for reducing the reward by an amount corresponding to the difference between the user's activity and the threshold.

For instance, as noted above, there may be multiple thresholds used in act 404 and compared against the user's physical activity. In one example there may be a minimum and maximum threshold. If the user does not meet the minimum threshold, then no reward may be provided. In contrast, the maximum threshold may correspond to a maximum reward so that once the maximum threshold is exceeded no additional rewards are provided. Anything between the minimum threshold and maximum threshold may correspond to a reward that is less than the full reward. The reward may be allocated proportionally, in a tiered manner, or in another format.

For instance, there may be tiers which corresponding to different thresholds, and a user may obtain rewards only upon meeting the additional thresholds to move from tier to tier. By way of example, if calories burned is the threshold criteria used and a maximum threshold is 2500 calories burned, there may be additional thresholds at 1000 calories burned, 1500 calories burned, and 2000 calories burned. Anything below 1000 calories burned may not provide any reward to the user. If the user burns between 1000 and 1500 calories, the user may receive twenty-five percent of a maximum reward. If the user burns between 1500 and 2000 calories, the user may receive fifty percent of the maximum reward. If the user burns between 2000 and 2500 calories, the user may receive seventy-five percent of the maximum reward, and the user can receive the full reward by exceeding 2500 calories.

The rewards available to the user as determined in act 406 may also be redeemed by the user. One manner of redeeming the rewards may include providing an interface through which the rewards can be selected, as provided in step 408. The interface may provide information on a single reward, or may allow a user to view multiple different reward options. As an illustration, if a television is connected in an exercise incentivizing system, the user may turn on the television, and potentially identify himself or herself. Upon doing so, the television may access information about the user's exercise activity and/or the rewards available based on exercise activity. When the rewards are determined, the user interface can identify the rewards that are available for redemption on the television, as shown in act 410. For instance, the television may indicate that based on the user's activity a certain amount of television watching time is available. The time may be tracked cumulatively, so that if a user previously redeemed a portion of the reward, the television may also display the time remaining for a redeemed reward.

Of course, for other devices subject to rewards, other options may be displayed. A gaming system, for instance, may indicate how much time is available for game play. A telephone may indicate how much talk time a person can redeem, how many text messages can be sent/received, or what portion of a full charge may be provided to the telephone, or what portion of a reward remains from an earlier redemption. Thus, each time a user accesses a system that may be operated in connection with an exercise incentivizing system, the user can be notified whether or not they have any time or other benefit remaining, or what rewards they can collect or redeem for use of the device. Often, the identification of the available rewards in act 410 may occur through a visual display; however, in other embodiments an audio or other display may be provided to indicate what reward is left. For instance, during a phone conversation an audio cue may play to indicate that a certain amount of time (e.g., 5 minutes) remains.

In accordance with some embodiments, the reward that is available may be less than a maximum reward. At least some embodiments contemplate advising the user that there are greater rewards available. Thus, in act 412 of step 408, a user may be notified that additional rewards are available and/or what the potential rewards may be. For instance, if a user is only receiving half of the maximum benefit, an audio or visual cue may identify the available reward as a percentage of the maximum, or may identify the maximum available reward. In some cases, the method 400 may also include providing encouragement to the user to earn greater rewards as shown in act 414. For instance, a message may be played or displayed that suggests to the user to continue exercising before redeeming the reward so that they can get a larger reward. If the user has earned a maximum reward, the encouragement provided in act 414 may be omitted, or may instead be congratulatory or encourage continued physical exercise in the future.

As shown in FIG. 4, the method 400 for rewarding a user that engages in physical activity can include accessing additional data in act 416. The act 416 can be performed in at virtually any stage of the method 400, and can include accessing data from different sources. For instance, when comparing physical activity of users to a threshold in act 404, the act 416 may be used to access the physical activity data, to access the thresholds, to obtain algorithms or functions for converting physical activity data to a value that can be compared to the thresholds, or the like. Similarly, to determine available rewards in act 406 additional data may be accessed in act 416 to determine what rewards are available. Additional data may also be accessed in act 416 during the step 408 for providing an interface for selecting rewards. The additional data may include what rewards are available or what maximum or other potential rewards are available. Messages to provide as encouragement in act 414 may also be available in act 416.

In some embodiments, the additional data accessed in act 416 may be keyed to certain criteria. For instance, to provide encouragement to a user to earn greater rewards in act 414, a system implementing the method 400 may provide contextually relevant information. Contextually relevant information may include such information as the weather, types of exercise the user enjoys or regularly engages in, and the like. As an illustration, the additional data accessed in act 416 may include information about the current weather conditions at the user's location. If the weather is suitable for outdoor activity, additional information may include what outdoor activities the user performs. If the weather is not suitable for outdoor activity, additional information may include what indoor activities the user regularly performs, or what nearby locations (e.g., a gym) the user can visit to continue exercising. Thus, on a sunny, warm day, a user who regularly jogs may be encouraged to go outside for a short jog to earn more rewards. On a cold, rainy day, a user who owns a treadmill may be encouraged to use the treadmill, or a user who is a member at a nearby gym may be encouraged to visit the gym to gain additional or greater rewards.

Optionally, the user interface includes a selection component through which the user can select to redeem a reward. In the method 400, user selection of a reward can be received as an instruction or message as shown by act 418 in which user selection of a reward is received. Following selection of a reward, the reward can be authorized and provided in act 420.

The selection and provision of rewards may be performed in various manners. For instance, a user may select a reward using an input/output component of a computing or other electronic device. A user interface may display a single reward or multiple rewards and the input/output component can be used in the selection. Upon receiving indication of the selection, the reward can be provided directly on the device where the selection is made, or a message may be sent. For instance, a message may be transmitted to a server or other computing system to account for rewards that are redeemed. In some embodiments selection of a reward may be automatic. For instance, by plugging in a telephone to charge, the telephone may automatically access information about what rewards are available and charge the device to the maximum allowed based on the rewards determined to be available in act 406.

As shown in FIG. 4, the method 400 can include the use of one or more thresholds to determine the rewards that are available to a user. The thresholds and rewards may be set in a number of manners. For instance, the thresholds may be programmatically determined and set by an author or provider of a computing program that executes all or a portion of the method 400 of FIG. 4. In other embodiments, thresholds may be dynamic based on research from medical or educational sources. In still other embodiments, an administrator may exercise some control over the thresholds as well as over the rewards.

Figure 5:
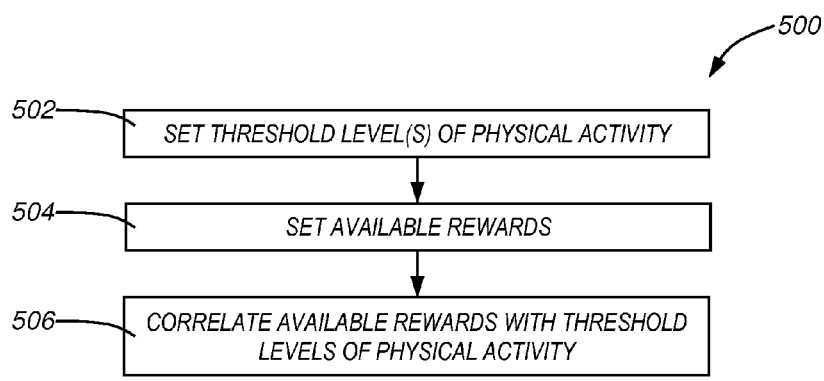
FIG. 5 illustrates a method for administrating exercise criteria and rewards for exercise according to an embodiment of the present disclosure.

FIG. 5 illustrates an example method 500 for administrating exercise criteria and rewards for exercise according to an embodiment of the present disclosure. In the method 500, one or more threshold levels of physical activity may be set in act 502. The threshold levels that are set may include any threshold as discussed or contemplated herein. Thus, a threshold may be set for categories such as exercise distance or duration, caloric expenditure (e.g., calories burned or a difference between calories consumed and burned), or the like. Moreover, multiple different thresholds can optionally be set, whether for categories of physical activity, or as multiple thresholds for the same physical activity. Further still, such thresholds may have different time constraints. As an illustration, some thresholds may be set for a particular period of time (e.g., a day, week month) while other thresholds may be for a different period of time. Indeed, the thresholds set in act 502 may even be varied day to day or month to month. For instance, one threshold may be set for weekdays while a different threshold is set for weekends.

One or more available rewards may also be set in act 504 of the method 500 of FIG. 5. Setting available rewards in act 504 may include identifying rewards that will be provided to a person satisfying all or portions of the physical activity thresholds identified in act 502. Such rewards may include identification of a device on which rewards can be redeemed as well as a value. For instance, a device may be a smart phone while a value may be a value for talk time, a number of text messages, an amount of charge to the battery, or the like.

In one embodiment, an administrator may know that a person whose physical activity is being tracked has access to a cellular phone, a gaming system, a desktop computer, a television, or other devices. If the administrator wants to control access to any or all such devices based on an exercise and incentive program, the administrator can specify rewards that correspond to each device. As discussed herein, rewards for a cell phone optionally relate to communication (e.g., talk time, text messaging, email availability, video conferencing, etc.), entertainment (e.g., music or game downloads or play), power supply, and the like. Similar rewards may be provided for other devices, and time available to play video games or watching television may thus also be set in act 504.

The thresholds set in act 502 and the rewards set in act 504 may also be correlated in an act 506. Such an act 506 may include indicating and/or storing a reward that is to be associated with a particular threshold. For instance, if a threshold of a particular number of calories burned is specified, that threshold can be associated with a particular reward for a cell phone, for example. The same threshold may also be correlated in act 504 with multiple different rewards. Thus, the same threshold for calories burned could be associated with a television viewing reward, a game play reward, or the like. Moreover, such rewards may be cumulative or exclusive. More particularly, if multiple rewards are associated with the same threshold, an administrator may be able to set whether the rewards are each available if the threshold is met (or based on what work towards the threshold is met), or whether the user may choose only one or less than all of the available rewards. Consequently, a user may be able to earn a reward for a certain amount of time for television viewing, video game playing, or talking on a cell phone; however, the user may not be able to redeem all of the rewards, but instead may only be able to redeem one reward, for example. In other embodiments, a user may be able to allocate the reward among different rewards. For instance, rather than redeeming a full amount of one reward, the user may redeem a portion of each of multiple rewards (e.g., 50% of the reward towards cell phone use, 25% towards television viewing and 25% towards video gaming).

Figure 7:
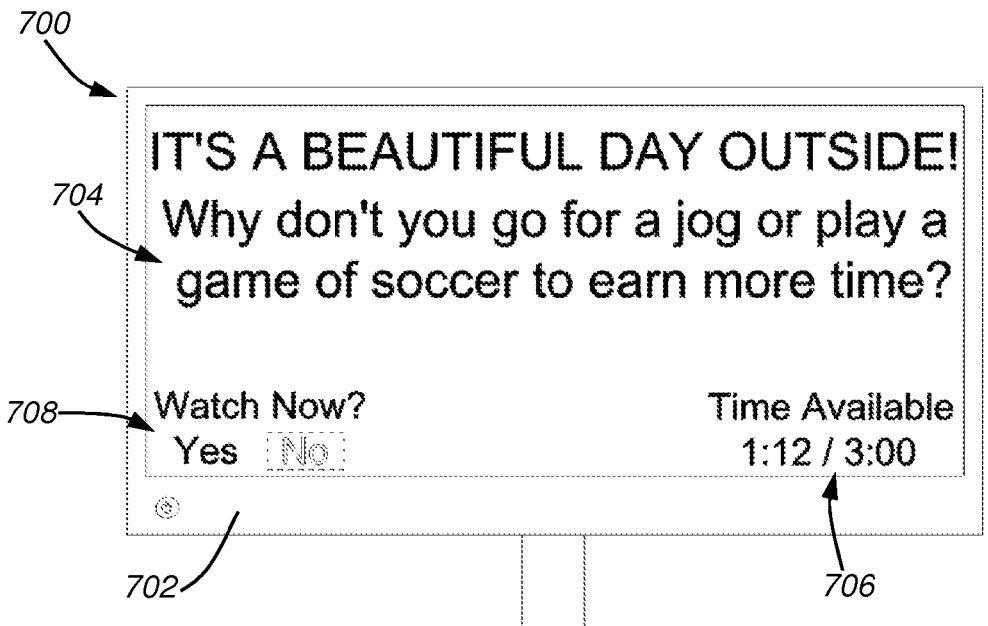
FIG. 7 illustrates an example television with a user interface providing a view for redeeming rewards associated with performance of physical exercise.
Figure 8:
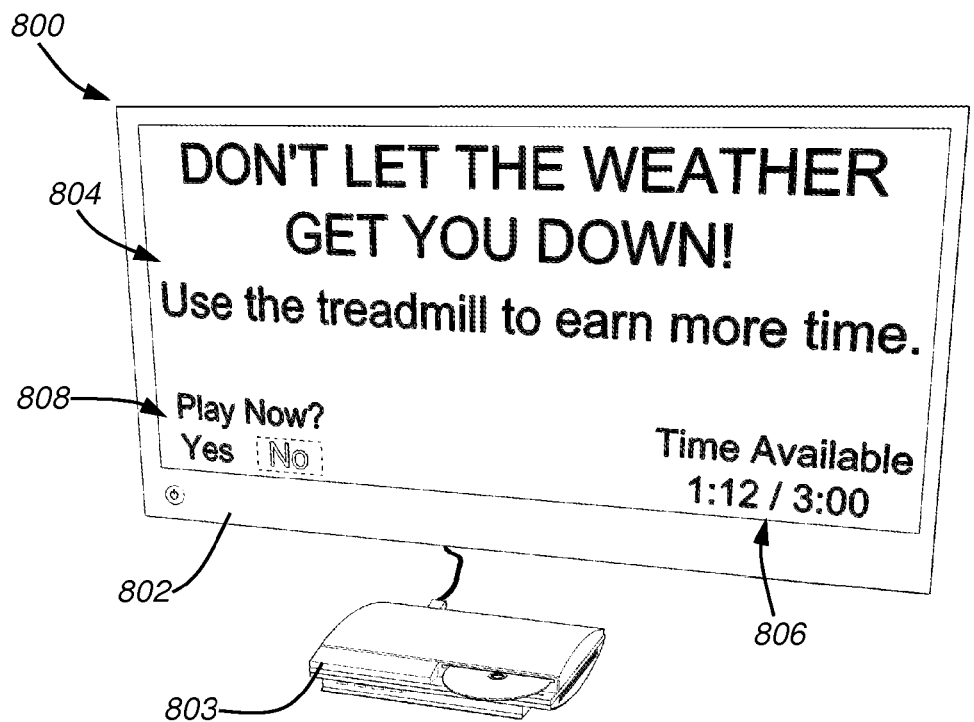
FIG. 8 illustrates an example video game system providing a view for redeeming rewards associated with performance of physical exercise.
Figure 9:
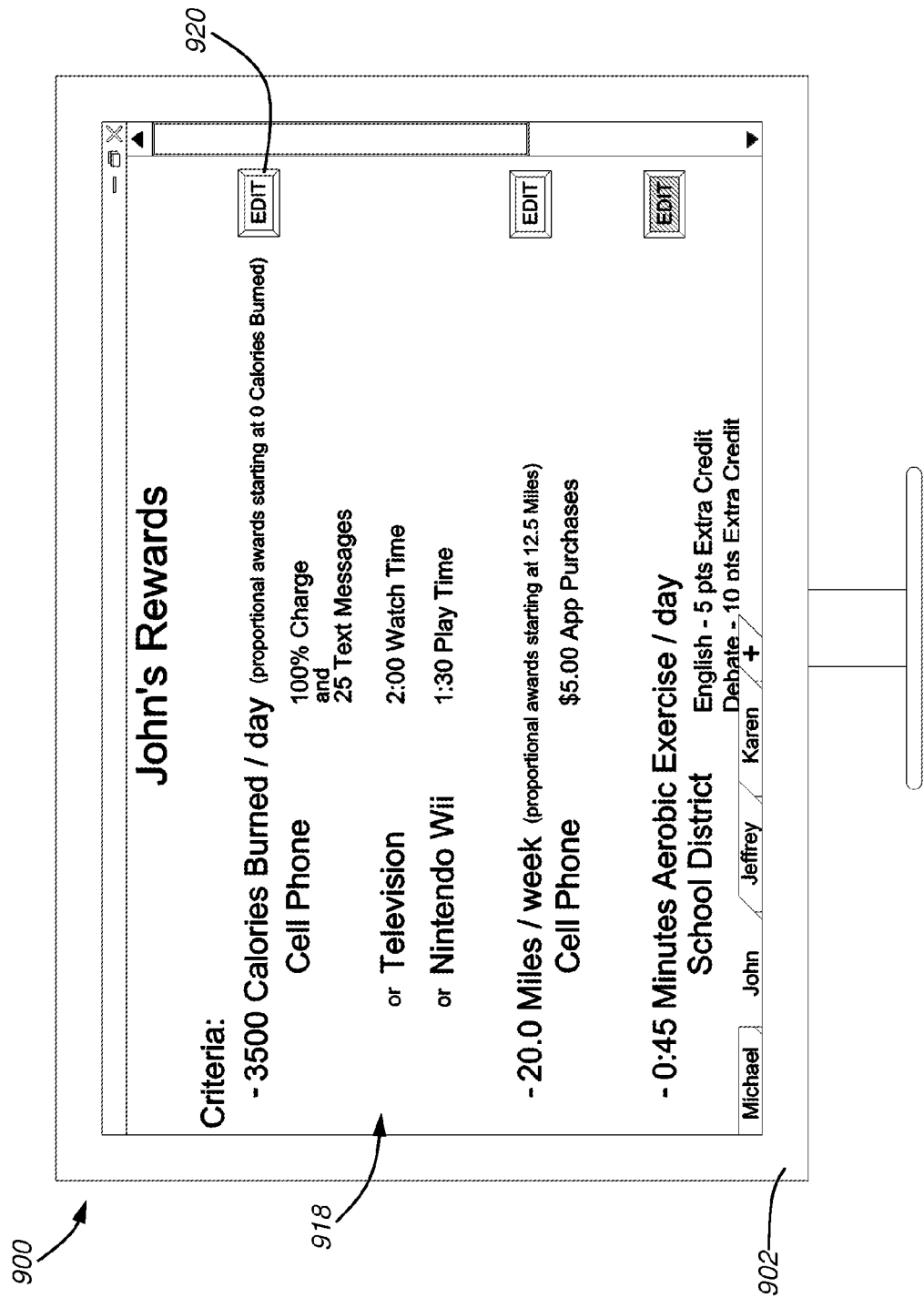
FIG. 9 illustrates an example display device including a user interface for an administrator of a system for incentivizing physical activity and exercise.

Turning now to FIGS. 6A-9, example embodiments of devices and interfaces for use in the performance of methods 400 and 500 of FIGS. 4 and 5 are illustrated in greater detail. In particular, FIGS. 6A-8 illustrate example devices and user interfaces at which physical activity and reward information may be provided and potentially selected, while FIG. 9 illustrates an example user interface for use by an administer of an exercise incentivizing system.

More particularly, FIGS. 6A-6E illustrate various views of an exercise and reward tracking system 600 in which a user interface 604 is displayed on an electronic device 602. In the illustrated embodiment, the electronic device 602 has the form of a portable electronic device such as a portable media player or smart phone; however, the electronic device 602 may include other devices, including laptops, desktop computing devices, gaming systems, televisions, tablet computing devices, and the like.

Figure 6A:
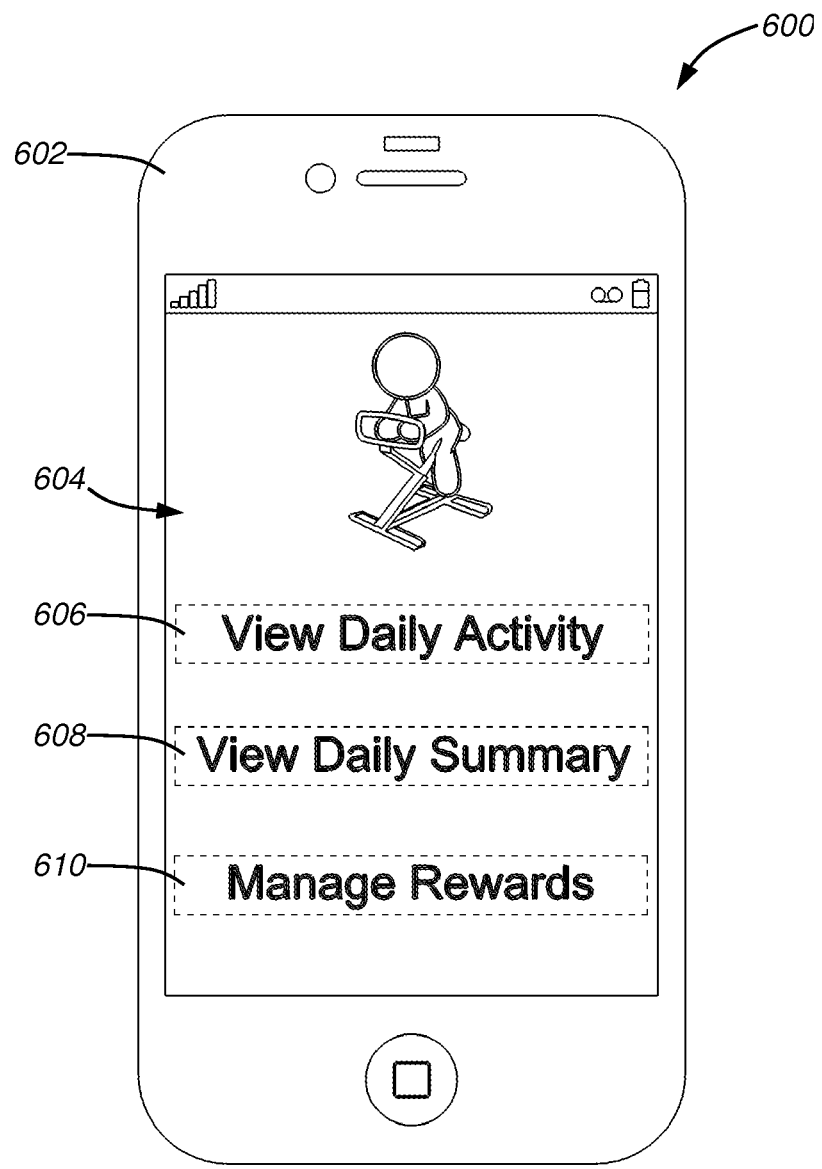
FIG. 6A illustrates an example computing device with a user interface providing a view for viewing exercise progress and managing rewards associated with performed exercise.

As shown in FIG. 6A, the user interface 604 may provide a user with various options to view information regarding the physical activity of a user, and potentially the rewards available to a user on account of physical activity of the user. The user interface 604 may be executed by a processor of the computing device 602 and can use information stored on the exercise device 602 and/or information obtained over a communication network from one or more remote sources. For instance, information stored on a server or sensing device may be accessed via wired or wireless communication connections and used by an application on the exercise device 602 to display the user interface 604.

In the illustrated embodiment, the menu view of the user interface 604 provides a user with multiple options. The illustrative options illustrated include an option 606 to view daily activity, an option 608 to view a daily summary, and an option 610 to manage rewards that may be available to the user of the device 602. Each of options 606-610 may be selected by the user to obtain a different view within the user interface 604. Of course, additional or different options may also be provided, including the option to manage or administer rewards as discussed herein.

Figure 6B:
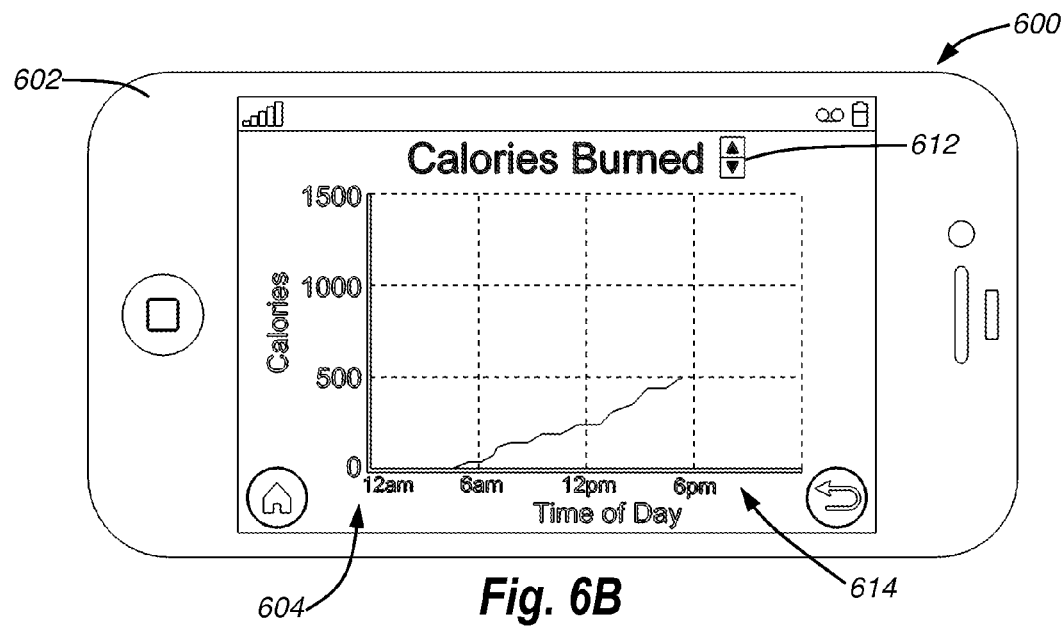
FIG. 6B illustrates the example computing device and user interface of FIG. 6A, while providing a view for graphically viewing performed exercise in terms of calories burned.

FIG. 6B illustrates an example view 614 of the user interface 604 that may be obtained to view a person's daily physical activity. In particular, the view 614 provides an option to view the number of calories burned by a person during a twenty-four hour period. In this embodiment, a graphical illustration depicts the number of calories burned using a graph to show an increase in calories burned during the day; however, other illustrations may also be used. For instance, a textual description of a number of calories burned may be provided. Other types of charts, graphs, descriptions and the like may also be provided.

A sensing device worn or carried by the user may obtain movement information that can be translated by the sensing device, the electrical device 602 or another device into the calories burned information. Other information may similarly be obtained by the sensing device and transferred within a communication network to the device 602. In one embodiment, a selector 612 within the user interface 604 allows a user to change the type of physical activity information is displayed. Thus, while a user may select to view calories burned, other information such as distance, average heart rate, steps taken, and the like may also be displayed. A sensing device may thus be able to track any number of different types of information related to physical activity, and the different types of information may be available to view on the device 602. Moreover, while a view 614 of the user interface 604 may display a single type of information, other embodiments contemplate multiple types of physical activity information in a single view.

Figure 6C:
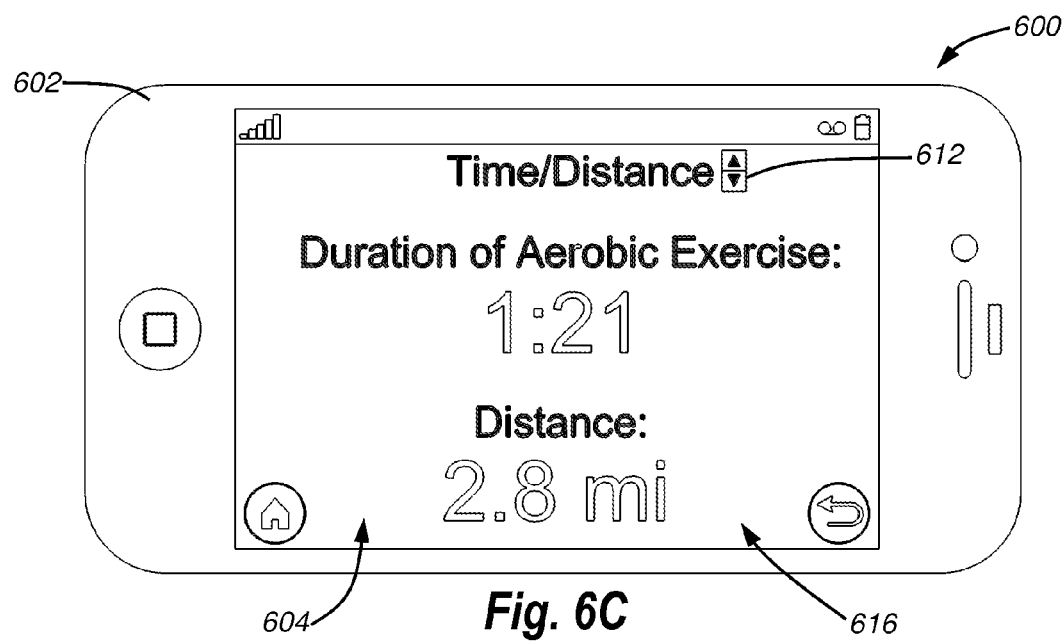
FIG. 6C illustrates the example computing device and user interface of FIG. 6A, while providing a view for viewing the duration and/or distance associated with performed exercise.

FIG. 6C, for instance, illustrates an alternative view 616 in the user interface in which the selector 612 has been used to show distance and duration information. More particularly, in this view 616 a duration component is displayed to describe the amount of time during a given period a user has engaged in aerobic exercise. In this case, the use engaged in one hour and twenty-one minutes of aerobic exercise. Such a determination may be based on heart rate to indicate how long during the day the user's heart rate was elevated beyond a particular rate.

The same view 616 of the user interface 604 may also display information such as distance. The distance information may correspond to the total distance a person traveled during a day, the distance traveled during a particular type of exercise (e.g., jogging or cycling), the distance traveled during aerobic exercise specified above, or it may represent any other distance that may be tracked directly by a sensing device, or indirectly using information obtained from a sensing or input device. Thus, while a single distance is displayed in the view 616, in other embodiments multiple distances may also be displayed.

Figures 6D, 6E:
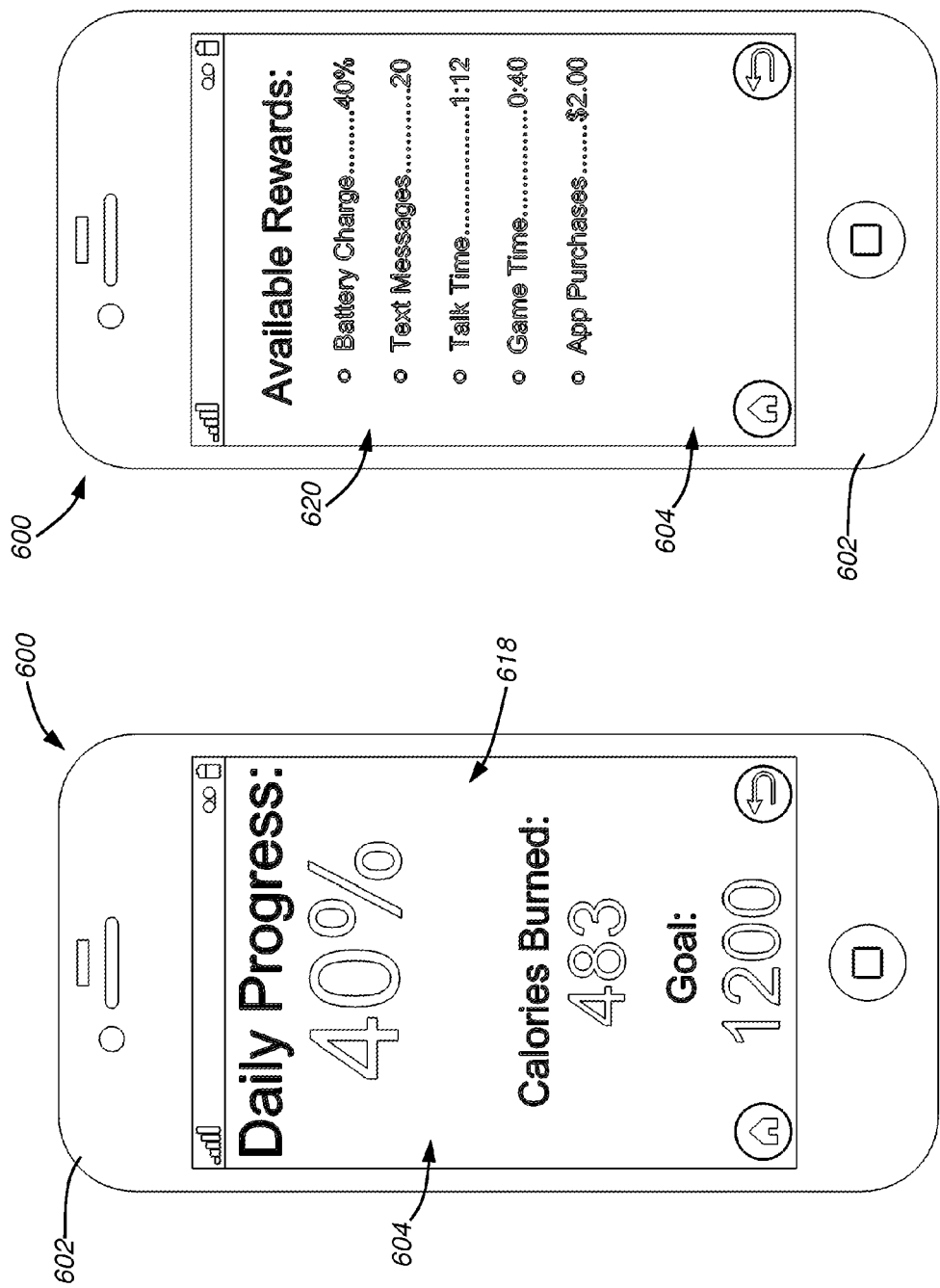
FIG. 6D illustrates the example computing device and user interface of FIG. 6A, while providing a view for viewing progress towards an exercise goal.
FIG. 6E illustrates the example computing device and user interface of FIG. 6A, while providing a view for viewing and/or selecting rewards that are available for exercise that has been performed.

The user interface 604 of FIGS. 6B and 6C may thus provide information obtained from a sensing device or other input device to allow a user to monitor his or her physical activity. As discussed herein, another aspect of monitoring a person's physical activity is the ability to obtain rewards based on the physical activity relative to a threshold. FIG. 6D, for instance, illustrates an example embodiment of a view 618 of the user interface 604, which view 618 provides a summary of activity relative to a particular threshold or goal. More particularly, the user of a sensing device may set a goal, or have a goal set for him or her. In this embodiment, the goal is to burn 1200 calories over a specified period of time. In the view 618 of FIG. 6D, the goal is displayed along with an indication of the number of calories burned thus far, which is in this case 483 calories. The user is thus about forty percent of the way towards completing the goal as is further specified in the view 618 of FIG. 6D. If there are multiple thresholds or levels set, a user may be able to move between various views to obtain a progress summary towards each goal. Alternatively, a single summary may provide information to track progress towards each of multiple fitness-related goals.

As described herein, a user may receive different rewards depending on whether the user has met a threshold or goal, or based upon the extent to which the user is nearing the goal. FIG. 6E illustrates an example embodiment of a view 620 of a user interface 604 which displays various rewards that may be available based on the progress a user has made towards a goal as shown in FIG. 6D.

More particularly, as shown in FIG. 6E, the user may be able to redeem various rewards. Some or all of the rewards may be redeemed directly for use of the electronic device

602, although other rewards may be redeemed for use with other devices or to provide other rewards. As shown in FIG. 6E, for instance, based on a comparison of the exercise performed to a threshold level desired, the user may be able to do a forty percent charge of the battery of the exercise device 602. Additionally, the user may be able to send and/or receive twenty text messages, talk for an hour and twelve minutes, play video games for forty minutes, or purchase up to two dollars worth of applications on the device 602. In some embodiments, the rewards are selectable so by selecting the particular reward (e.g., using a touch-screen or cursor-based input device) the user can redeem the reward. If, for instance, a user selects to redeem the reward to charge the battery, the user can connect the electronic device 602 to a power source and an application executing on the device 602 will monitor the power charge. When the charge has reached forty percent, or potentially been increased by forty percent, the application may cause the battery to stop charging.

Similarly, if a user selects to redeem a reward for text messages, the application on the electronic device 620 may monitor incoming and outgoing text messages. Once a message total reaches twenty it may disable the text messaging application. Gaming applications, phone systems and application purchasing systems on the device 602 may be subjected to similar controls. The various rewards may be cumulative so that the user can redeem each of the rewards; however, in other embodiments the user may select only one or less than all rewards. For instance, a user may be able to select to use the phone functions of the electronic device 602 or the game playing functions, but not both. In other embodiments, the user can allocate rewards among multiple devices. As an example, rather than redeeming the full one hour twelve minutes of talk time, the user may use thirty-six minutes. By using only half the available talk time, the user could then potentially select to play games for twenty minutes, or half the available gaming time. Thus, some embodiments may also contemplate automatic redemption of rewards. In such embodiments, the user interface 604 or the application executing the user interface could cause a reward to be redeemed by a user using the device in a particular manner (e.g., by using the telephone functions) rather than selecting a particular reward beforehand. In such an embodiment, the user interface 604 could optionally display the time remaining for the reward or for other rewards where a reward can be allocated among multiple redemption possibilities.

FIG. 7 illustrates another example of a system 700 in which rewards can be redeemed as a result of physical activity. In the illustrated embodiment, the system 700 includes a television 700. The television 700 may have an application or other program executing thereon which controls the availability of access to the television. Optionally, the application can execute or display a user interface 704 to provide the user with information about his or her rewards.

In FIG. 7, for instance, the user interface 704 may be displayed when a user turns on the television 704. Once turned on, the television 704 may be used to determine whether the user requesting to view television has performed sufficient exercise or has any rewards left to allow television viewing to continue. The television 704 may thus communicate with a sensing device, a server, another computing device, or some other component. Information that is obtained can then be used to display information about rewards. In FIG. 7, for instance, a reward 706 is displayed. The illustrated reward 706 indicates that the user has one hour and twelve minutes of a maximum three hours television viewing time available. The user may then use a selection mechanism 708 to begin watching television to start redeeming the reward. If the user stops watching television 702, the application on the television 702 (or on a set-top-box or controller connected to the television 702) may stop the time from running so that the next time the user turns on the television the time available and/or maximum time available may be decreased to show how much time is left and how much more could potentially be earned.

More specifically, as described herein, rewards for exercise may not only be established for meeting a particular threshold or goal, but for progress towards a goal. Thus, upon reaching or exceeding the threshold, the user may obtain the full reward. If, however, the user has only progressed partially towards the threshold, less than the full reward may be available, whether in a stepped, tiered, or other allocation scheme. For instance, if a user has made forty percent progress towards a goal, the user could receive forty percent of the reward, which in this embodiment may be time for television watching.

According to one embodiment of the present disclosure, although a user may redeem a partial reward, systems contemplated may nonetheless continue to encourage a person to continue exercising to maximize his or her rewards. The user interface 704 of FIG. 7, for instance, includes an encouragement to play soccer or go for a jog to earn more time. The encouragement may be tailored to the person and/or other factors. For instance, the encouragement also indicates that there is beautiful weather outdoors. As discussed herein, systems and methods of the present disclosure contemplate accessing external resources to obtain certain information. The application on the television 702 may, for instance, access a weather system database to determine what weather conditions are like. If there is suitable weather, the user can be encouraged to exercise outdoors, similar to the manner suggested in FIG. 7. Further information stored on the television 702 or accessible thereto may also indicate that the user enjoys or regularly engages in jogging or soccer. Consequently, the user interface 704 may recommend activities the user enjoys. Alternatively, other activities may also be suggested to try and expand the types of activities the user participates in, although in some embodiments encouragement may be provided without recommending a particular activity.

A similar exercise incentivizing system is illustrated in FIG. 8 in the context of a gaming system 800. In this embodiment, the system includes a display 802 connected to a gaming unit 803. The gaming unit 803 may also be executing or have access to an application which is used to control the function of the gaming unit 803 based on rewards offered to a user. As discussed herein, such rewards may be provided based on the physical activity of a user wanting to use the gaming system 800.

In the illustrated embodiment, the application used by the gaming unit 803 may produce a user interface 804 for the display 802. The user interface 804 may display various types of information, including information about rewards available. In this case, a reward 806 is indicated as an amount of time available for game playing, and the reward 806 optionally includes information about the maximum time that could be earned.

The user interface 804 may also encourage the user to continue exercising. Where, as here, the user has not maximized his or her reward, the user interface 804 may display a message telling the user to continue exercising. In this particular embodiment, weather information may be accessed to determine that poor weather exists in the area.

As a result, the user is encouraged to exercise indoors, such as by using a treadmill. If the user decides to earn more time, the user can select the "No" option on the selection mechanism 808; however, the user can begin redeeming the rewarded play time using the alternative "Yes" option.

FIG. 9 illustrates an alternative embodiment of a system 900 that may be used to incentivize people to exercise and be physically active. Whereas systems 600-800 of FIGS. 6A-8 generally correspond to end-user systems that may be used to view and redeem rewards, the system 900 of FIG. 9 instead illustrates an example system that may be used to administer a rewards system.

In particular, the illustrated embodiment includes a user interface 918 that may be displayed on a display device 902. As will be appreciated in view of the disclosure herein, the example user interface 918 may be produced by using a computing system connected to the display device 902. In some embodiments the application may be a local application, although the application may also be distributed. For instance, the application used to produce the user interface 918 may implemented in a cloud-based system so that a browser application may be used to access information processed primarily remote from the display device 902.

As discussed herein, incentives to exercise may be provided by a parent, guardian, educator, or other person or entity capable of administering an incentive program. For instance, a parent may exercise some control over the various different electronic devices used by his or her children, and can use a reward system as described herein to grant or deny access to one or more devices, to limit the use of such devices, and the like. FIG. 9, for instance, illustrates an embodiment similar to what may be viewed or provided to a parent. In this embodiment, there may be four children. Using an exercise administration application, the parent may establish different thresholds or goals that the children must meet for certain usage privileges.

The system 900 of FIG. 9 contemplates that one of the children is John, and that John may have access to various electronic devices, including a cell phone, television, and a gaming system. The parent or other administrator has, in this embodiment, set-up thresholds for use in providing various different rewards. More particularly, if the user is able to burn 3500 calories in a day, the user may obtain cell phone, television, or gaming system access. In particular, in this embodiment, the system is set-up to provide a full charge and twenty-five text messages for the cell phone if the calorie burned threshold is satisfied. As alternative rewards, John could instead earn two hours of television watching time, or an hour and a half of game playing time.

As also shown in the user interface 918 of FIG. 9, the rewards may be proportionally applied. In this particular embodiment, a proportional reward is allowed starting at zero calories all the way up to 3500 calories. Thus, if John was to burn 2800 calories, he could earn eighty percent of the identified rewards. As also shown in FIG. 9, a control 920 may be provided to allow the administrator to edit the criteria, rewards, or allocation of the rewards at any time.

Multiple criteria or thresholds may also be set for a single person, as shown in FIG. 9. For instance, in the illustrated embodiment, an administrator may be able to set a daily threshold for burned calories, as well as a weekly threshold for distance run or otherwise covered during exercise. If John satisfies the threshold, additional rewards may be earned, which in this case may be a monetary amount towards the purchase of applications for John's cell phone. The rewards may be proportionally applied only after reaching a certain level, although other allocation schemes may also be offered. Of course, the illustrated rewards and criteria are merely illustrative and other rewards may also be available.

For instance, as shown in FIG. 9, additional rewards may be available to benefit John's in school. In the illustrated embodiment, for instance, if John satisfies a requirement for exercising forty-five minutes a day, the user interface 918 may notify the school district of his performance. As a result of such notification, extra credit may be obtained in various classes. In some cases, the parent or administrator controlling access to electronic devices may not be able to also specify the rewards for entities, such as a school. In FIG. 9, for instance, the option to edit the scholastic rewards has been grayed out. Thus, an administrator is optionally notified of rewards available to the same person being monitored even if the administrator cannot modify those rewards. In other embodiments, the administrator may not have any access to the reward information from other entities.

While FIG. 9 illustrates the reward and threshold values and criteria for one person (i.e., John), the same user interface 918 may be used to administer a reward system for multiple users. In particular, in tabs shown in FIG. 9, three other users may have reward systems set-up, and the option to add still other participants is included. Each participant may have different rewards, different thresholds, or a combination thereof. Alternatively, each participant may have the same general rewards and/or thresholds.

Embodiments of the present disclosure may generally be performed by a computing device, and more particularly performed in response to instructions provided by an application executing on the computing device or system, including systems that are distributed with both local and remote resources. Therefore, embodiments of the present disclosure may run on general purpose or special purpose computing devices once a suitable application is installed. In other embodiments, a cloud-based or software-as-a-service system, or hardware, firmware, software, or any combination of the foregoing may be used in directing the operation of a computing device or system.

Embodiments of the present disclosure may thus comprise or utilize a special purpose or general-purpose computer including computer hardware, such as, for example, one or more processors and system memory, as discussed in greater detail herein. Embodiments within the scope of the present disclosure also include physical and other computer-readable media for carrying or storing computer-executable instructions and/or data structures, including applications, tables, or other modules used to execute particular functions or direct selection or execution of other modules. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the disclosure can comprise at least two distinctly different kinds of computer-readable media, including at least computer storage media and/or transmission media.

Examples of computer storage media include RAM, ROM, EEPROM, CD-ROM or other optical disk storage, magnetic disk storage or other magnetic storage devices, or any other non-transmission medium which can be used to store desired program code means in the form of computer-executable instructions or data structures and which can be accessed by a general purpose or special purpose computer.

When information is transferred or provided over a communication network or another communications connection (either hardwired, wireless, or a combination of hardwired or wireless) to a computing device, the computing device properly views the connection as a transmission medium. Transmissions media can include a communication network and/or data links, carrier waves, wireless signals, and the like, which can be used to carry desired program or template code means or instructions in the form of computer-executable instructions or data structures and which can be accessed by a general purpose or special purpose computer. Combinations of physical storage media and transmission media should also be included within the scope of computer-readable media. Further, upon reaching various computer system components, program code means in the form of computer-executable instructions or data structures can be transferred automatically from transmission media to computer storage media (or vice versa). Thus, it should be understood that computer storage media can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or source code. Although the subject matter has been described in language specific to structural features and/or methodological acts, it is to be understood that the subject matter defined in the appended claims is not necessarily limited to the described features or acts described above, nor performance of the described acts or steps by the components described above. Rather, the described features and acts are disclosed as example forms of implementing the claims.

Those skilled in the art will appreciate that the embodiments may be practiced in network computing environments with many types of computer system configurations, including, personal computers, desktop computers, laptop computers, message processors, hand-held devices, programmable logic machines, multi-processor systems, microprocessor-based or programmable consumer electronics, network PCs, tablet computing devices, minicomputers, mainframe computers, mobile telephones, PDAs, servers, watches, portable chips, and the like.

INDUSTRIAL APPLICABILITY

In general, the exercise incentivizing systems, devices and methods of the present disclosure relate to monitoring physical activity performed by a person and providing rewards based on the extent of such physical activity. Specifically, a person may go throughout the day engaging in various types of activities, which activities may have varying levels of physical strain. A sensing device worn or carried by the user may detect how much the person moves, the user's heart rate, and other factors related to physical activity. Based on such information, a profile of the person may be obtained with information that includes the activities engaged in, the number of calories burned, the duration of exercise, distance traveled during one or more types of exercise, and the like.

A parent or guardian may be particularly interested in monitoring the exercise and physical activity of children. For instance, a parent may use the physical activity information gathered by a sensing device to determine whether a child will be allowed to use another device. An automated system may therefore be provided to allow a child to watch television, play video games, use a cell phone, and the like only if the child engages in a suitable amount of physical activity. The parent or guardian may specify what level of activity is required, and can do so over a period of time with a user-defined granularity. Thus, a user may want to incentivize exercise during a particular time of day, over a full day, week, month, or the like.

If the user is able to reach the defined threshold of physical activity, the user can receive the rewards set-up by the parent or guardian. For instance, a parent may limit use of a cell phone, television, or gaming system. If a reward is earned, additional time may be provided to use those devices or systems. Other rewards may also be provided, including monetary rewards. In another example, a portable device may have its power capacity limited. For instance, if a child doesn't satisfy an exercise threshold, the child may be unable to charge his or her cell phone. The rewards provided may be cumulative, although in some cases they are awarded on a time-limited basis so that if not used during a particular period they are lost. Parents, for example, may want to limit television watching and grant awards on a daily basis so a child cannot save rewards to watch no television one day and an excessive amount the next.

By comparing actual physical activity to a threshold, the entitlement of child to a reward may be determined. Additional aspects contemplate providing rewards even when the threshold is not met. For instance, as a user progresses towards a threshold, rewards may be provided in proportion to the user's progress. Thus, if a user is half way to reaching the threshold, the rewards may be available but cut in half.

Embodiments also contemplate allowing parents and other administrators to ensure that the applications and programs used in an exercise incentivizing program are operating correctly and efficiently. In some embodiments, rewards may relate to use of electronic devices, and control of those electronic devices may be monitored by an application executing on the device. Monitoring systems on an administrative-side system may from time-to-time evaluate performance of the applications, and may ensure that such applications remain installed and have not been tampered with to avoid controls established by the administrator. If the application ceases operation or is disabled, the administrator can be notified to take corrective action.

Where a reward relates to the charge or use of a communication device, override capabilities may also be enforced. For instance, if a child has used all of the talk time on a cellular phone, a parent may nevertheless be able to override the system to get in contact with the child or allow the child to contact the parents. Exceptions may be provided to ensure that communication with the parents or certain others may occur uninterrupted regardless of the rewards and device usage limits. In a similar manner, if a cell phone or other device is provided a limited charge, a portion of that charge, or an additional charge, may be held in reserve to allow operation of the device to get in contact with the parents or others. In some cases, a reward for a limited charge may not actually limit the amount of charge provided to the phone or other device. Instead, an application may monitor the charge on a battery. When the battery charge has reduced by a certain amount (e.g., if battery power drops from 100% to 50% and a user has a 50% battery charge reward), an application may disable certain functions of the device.

While parents may be administrators to control rewards and define physical activity thresholds for the rewards, others may also act as administrators. For instance, insurance companies, cell-phone providers, or employers may allow people to opt-in to monitoring systems and provide benefits associated with wellness programs they administer. Additionally, schools may allow students to enroll in systems monitoring physical activity. As has been reported by authors of various studies, there is a significant and positive correlation between physical activity and scholastic performance. A review of fourteen such studies was conducted and produced in the January 2012 volume of the Archives of Pediatrics & Adolescent Medicine. As highlighted in the publication, children who are more physically active have improved academic performance, which is likely the result of improved cognition, decreased stress and increased nerve cell creation and support of synaptic plasticity. With the positive correlation between physical activity and academic performance, schools may administer a program whereby extra credit or other incentives can be provided based on the physical activities of enrolled children.

Systems and methods of the present disclosure are also contemplated for use with existing systems and across multiple platforms. For instance, a person may track his or her activity online. For instance, the WWW.IFIT.COM website allows users to track workouts and nutritional information. Embodiments contemplated herein may interface with the WWW.IFIT.COM or other websites to automatically update such websites with information, or to access information from such websites. As an example, a workout tracking website may maintain fitness information such as weight, height, and the like. A sensing device may access the website to obtain such physical information to calculate the number of calories burned over a period of exercise, or can even provide the workout information to the website so the website can calculate the calories burned information.

Further still, different systems may concurrently monitor a person's physical activity and provide different rewards. For instance, as discussed herein, a parent may monitor a child's activity and a school may monitor the same activity. Different rewards may be provided for the same activity by each administrator. A fitness tracking website, employer, or other person or entity may also track such information to provide still additional rewards. Each administrator may have access to only his or her information—or may be able to view other information for the same person being tracked—but each user can potentially monitor the rewards available from all program administrators. Such monitoring may be on a single application or interface or on multiple applications and interfaces.

What is claimed is:

1. A method for incentivizing physical activity, comprising:
   in a computing system that includes one or more processors;
      tracking a person's physical activity over a period of time;
      comparing the person's physical activity to a threshold for the period of time;
      identifying a reward corresponding to the threshold, the reward comprising use of an electronic device; and
      determining that the person's physical activity is less than the threshold and, in response, authorizing a proportional amount of the reward, the proportional amount being scaled based on the person's physical activity relative to the threshold;
      wherein authorizing the proportional amount of the reward comprises authorizing a battery charge of the electronic device, the authorized battery charge being less than a full charge of the battery.

2. The method recited in claim 1, wherein tracking person's physical activity includes obtaining data from a sensing device carried or worn by the person.

3. The method recited in claim 1, wherein comparing the person's physical activity to a threshold includes comparing a number of calories burned to a threshold number of calories burned.

4. The method recited in claim 1, wherein the threshold includes one or more of a distance or duration.

5. The method recited in claim 1, wherein comparing the person's physical activity to a threshold includes comparing the person's physical activity to a plurality of thresholds.

6. The method recited in claim 5, wherein the plurality of thresholds correspond to a same reward.

7. The method recited in claim 5, wherein the plurality of thresholds correspond to different rewards.

8. The method recited in claim 1, further comprising:
   restricting the battery charge based on a proportion of the person's physical activity relative to the threshold.

9. The method recited in claim 1, wherein the reward includes one or more of:
   talk time;
   text messaging;
   email messages; or
   video game playing time.

10. The method recited in claim 1, wherein identifying a reward corresponding to the threshold includes identifying a plurality of rewards corresponding to the threshold.

11. The method recited in claim 10, wherein authorizing the reward includes authorizing the plurality of rewards, the plurality of rewards collectively being proportional to the person's physical activity relative to the threshold.

12. A system for incentivizing physical activity of a user, the system comprising:
   a sensing device that tracks physical activity of a user; and
   a computing device with one or more processors that receives information from the sensing device regarding the physical activity of the user, the computing device comparing the physical activity of the user with a threshold, the computing device identifying a reward based upon comparing the physical activity of the user with the threshold, the reward comprising a limited amount of power to power an electronic device, the computing device determining the limited amount of power to power the electronic device based upon a proportional amount of the physical activity of the user relative to the threshold.

13. The system recited in claim 12, wherein the limited amount of power to power the electronic device comprises authorizing a battery charge of the electronic device.

* * * * *